United States Patent
Nagamori et al.

(10) Patent No.: US 9,839,701 B2
(45) Date of Patent: *Dec. 12, 2017

(54) AROMATIC AMINO ACID DERIVATIVE AND POSITRON EMISSION TOPOGRAPHY (PET) PROBE USING THE SAME

(71) Applicants: OSAKA UNIVERSITY, Osaka (JP); NARD INSTITUTE, LTD., Hyogo (JP)

(72) Inventors: Shushi Nagamori, Osaka (JP); Yoshikatsu Kanai, Osaka (JP); Hidekazu Nakao, Hyogo (JP); Tokutaro Ogata, Hyogo (JP)

(73) Assignees: OSAKA UNIVERSITY, Osaka (JP); NARD INSTITUTE, LTD., Hyogo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/766,826

(22) PCT Filed: Feb. 10, 2014

(86) PCT No.: PCT/JP2014/053100
§ 371 (c)(1),
(2) Date: Oct. 19, 2015

(87) PCT Pub. No.: WO2014/126071
PCT Pub. Date: Aug. 21, 2014

(65) Prior Publication Data
US 2016/0038620 A1 Feb. 11, 2016

(30) Foreign Application Priority Data
Feb. 12, 2013 (JP) .................. 2013-024810
Nov. 20, 2013 (JP) .................. 2013-240126

(51) Int. Cl.
| | | |
|---|---|---|
| A61K 51/04 | (2006.01) | |
| C07C 229/36 | (2006.01) | |
| C07C 323/63 | (2006.01) | |
| C07D 295/096 | (2006.01) | |
| C07C 309/73 | (2006.01) | |

(52) U.S. Cl.
CPC ........ A61K 51/0402 (2013.01); C07C 229/36 (2013.01); C07C 309/73 (2013.01); C07C 323/63 (2013.01); C07D 295/096 (2013.01); C07B 2200/05 (2013.01); C07C 2101/02 (2013.01); C07C 2101/04 (2013.01); C07C 2101/08 (2013.01); C07C 2101/14 (2013.01)

(58) Field of Classification Search
CPC .................................................. A61K 51/0402
USPC ........................................................ 424/1.89
See application file for complete search history.

(56) References Cited

U.S. PATENT DOCUMENTS

| | | | |
|---|---|---|---|
| 4,716,113 A | 12/1987 | Urban | |
| 8,907,126 B2* | 12/2014 | Nakao | .............. C07C 227/16 |
| | | | 562/444 |
| 2004/0192954 A1 | 9/2004 | Hamacher | |
| 2005/0119256 A1 | 6/2005 | Endo et al. | |
| 2006/0127306 A1* | 6/2006 | Mertens | .................. 424/1.11 |

(Continued)

FOREIGN PATENT DOCUMENTS

| | | |
|---|---|---|
| JP | 61-57588 | 3/1986 |
| JP | 2004-529989 | 9/2004 |

(Continued)

OTHER PUBLICATIONS

Shikano et al. Nucl. Med. Biol. 2010, 27, 903-910.*
MingWei et al. Sci. Chin Ser. B: Chem. 2007, 50, 276-283.*
Tsukada et al. Eur. J. Nucl. Med. Mol. Imag. 2006, 33, 1017-1024.*
De Jesus et al. J. Labelled Cmpd Radiopharm. 1998, 189-194.*
Krummeich et al. Appl. Radiat. Isot. 1994, 45, 929-935.*
Zhang et al. Curr. Top. Med. Chem. 2007, 7, 1817-1828.*

(Continued)

*Primary Examiner* — Michael G Hartley
*Assistant Examiner* — Sean R Donohue
(74) *Attorney, Agent, or Firm* — Wenderoth, Lind & Ponack, L.L.P.

(57) ABSTRACT

A compound having a structure represented by the general formula (I):

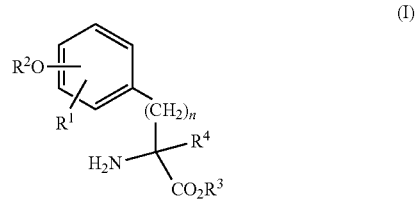

(wherein n is 0 or 1;
$R^1$ represents a hydrogen atom (only if n=0), a halogen atom, a C1-C6 alkyl group, a C1-C6 haloalkyl group, an optionally substituted amino group, an optionally substituted phenyl group, a C1-C6 alkylthio group, a C1-C6 alkoxy group, a C1-C6 haloalkoxy group or a C7-C12 aralkyloxy group;
$R^2$ represents $-(CH_2)_p-[O(CH_2)_q]_r-X$ (wherein X is a halogen atom, p is an integer of 1 to 6, q is an integer of 1 to 4, and r is an integer of 0 to 4);
$R^3$ represents a hydrogen atom, a C1-C6 alkyl group, a C7-C16 aralkyl group or a C6-C14 aryl group; and
$R^4$ represents a hydrogen atom or a C1-C6 alkyl group), or a pharmaceutically acceptable salt thereof excels FAMT in terms of the tendency to accumulate intensively in cancer, the affinity for LAT1 and the selectivity for cancer, and can be labeled using an automated synthesizer in clinical settings, and therefore is useful as a highly versatile PET imaging agent.

14 Claims, 3 Drawing Sheets

(56) References Cited

U.S. PATENT DOCUMENTS

| | | | |
|---|---|---|---|
| 2007/0031328 A1* | 2/2007 | Kung | A61K 47/48215 424/1.11 |
| 2008/0138281 A1 | 6/2008 | Sugiyama et al. | |
| 2009/0098048 A2 | 4/2009 | Sato et al. | |
| 2011/0150767 A1 | 6/2011 | Wempe et al. | |
| 2012/0171119 A1 | 7/2012 | Mach et al. | |

FOREIGN PATENT DOCUMENTS

| | | |
|---|---|---|
| JP | 2007-112725 | 5/2007 |
| JP | 4705756 | 3/2011 |
| WO | 03/066574 | 8/2003 |
| WO | 2005/115971 | 12/2005 |
| WO | 2012/025464 | 3/2012 |

OTHER PUBLICATIONS

International Preliminary Report on Patentability dated Mar. 24, 2014 in International (PCT) Application No. PCT/JP2014/053100, English translation.

International Search Report dated Apr. 1, 2014 in International (PCT) Application No. PCT/JP2014/053100.

Escoula et al., "A New Method for Iodine-Labelling of DOPA", New Journal of Chemistry, vol. 15, No. 1, 1991, pp. 75-78.

Database STN Registry [Online], RN 1213376-09-0, 2010, [retrieved on Mar. 18, 2014].

Database STN Registry [Online], RN 1213143-93-1, 2010, [retrieved on Mar. 18, 2014].

Database STN Registry [Online], RN 1381957-82-9, 2012, [retrieved on Mar. 18, 2014].

Database STN Registry [Online], RN 1259992-36-3, 2011, [retrieved on Mar. 18, 2014].

Database STN Registry [Online], RN 1259984-30-9, 2011, [retrieved on Mar. 18, 2014].

Database STN Registry [Online], RN 1259980-36-3, 2011, [retrieved on Mar. 18, 2014].

Database STN Registry [Online], RN 1381960-16-2, 2012, [retrieved on Mar. 18, 2014].

Database STN Registry [Online], RN 1259963-93-3, 2011, [retrieved on Mar. 18, 2014].

Kaira et al., "Fluorine-18-α-Methyltyrosine Positron Emission Tomography for Diagnosis and Staging of Lung Cancer: A Clinicopathologic Study", Clinical Cancer Research, vol. 13, No. 21, Nov. 1, 2007, pp. 6369-6378.

Kanai et al., "Expression Cloning and Characterization of a Transporter for Large Neutral Amino Acids Activated by the Heavy Chain of 4F2 Antigen (CD98)", The Journal of Biological Chemistry, vol. 273, No. 37, Sep. 11, 1998, pp. 23629-23632.

Wiriyasermkul et al., "Transport of 3-Fluoro-$_L$-α-Methyl-Tyrosine by Tumor-Upregulated L-Type Amino Acid Transporter 1: A Cause of the Tumor Uptake in PET", The Journal of Nuclear Medicine, vol. 53, No. 8, Aug. 2012, pp. 1253-1261.

Bergstrom et al., "Discrepancies in Brain Tumor Extent as Shown by Computed Tomography and Positron Emission Tomography Using [$^{68}$Ga]EDTA, [$^{11}$C]Glucose, and [$^{11}$C]Methionine", Journal of Computer Assisted Tomography, vol. 7, No. 6, Dec. 1983, p. 1062-1066.

Khunweeraphong et al., "Establishment of Stable Cell Lines With High Expression of Heterodimers of Human 4F2hc and Human Amino Acid Transporter LAT1 or LAT2 and Delineation of Their Differential Interaction With α-Alkyl Moieties", J Pharmacol Sci, 119: 368-380 (2012).

Strauss et al. (eds.), Zeglis et al., "Radiopharmaceuticals for Imaging in Oncology with Special Emphasis on Positron-Emitting Agents", Nuclear Oncology: Pathophysiology and Clinical Applications, pp. 35-78 (2013).

Limin Wang et al.; "Synthesis and in vitro evaluation of $^{18}$F labeled tyrosine derivatives as potential positron emission tomography (PET) imaging agents", Bioorganic and Medicinal Chemistry Letters, vol. 20, (2010) pp. 3482-3485.

Aristeidis Chiotellis et al.; "Synthesis and Biological Evaluation of $^{18}$F-Labeled Fluoroethoxy Tryptophan Analogues as Potential PET Tumor Imaging Agents", Molecular Pharmaceutics, vol. 11 (11), (2014) pp. 3839-3851.

Hideo Tsukada et al.; "Evaluation of D-isomers of O-$^{18}$F-fluoromethyl, O-$^{18}$F-fluoroethyl and O-$^{18}$F-fluoropropyl tyrosine as tumour imaging agents in mice", European Journal of Nuclear Medicine and Molecular Imaging, vol. 33 No. 9, Sep. 2006, pp. 1017-1024.

Misato Takashima-Hirano et al.; "Efficient sequential synthesis of PET probes of the COX-2 inhibitor [$^{11}$C] celecoxib and its major metabolite [$^{11}$C] SC-62807 and in vivo PET evaluation", Bioorganic and Medicinal Chemistry, vol. 19, (2011), pp. 2997-3004.

Misato Takashima-Hirano et al.; "General method for the $^{11}$C-Labeling of 2-Arylpropionic Acids and Their Esters: Construction of a PET Tracer Library for a Study of Biological Events Involved in COXs Expression", Chemistry European Journal, vol. 16, (2010), pp. 4250-4258.

* cited by examiner

AROMATIC AMINO ACID DERIVATIVE AND POSITRON EMISSION TOPOGRAPHY (PET) PROBE USING THE SAME

TECHNICAL FIELD

The present invention relates to an aromatic amino acid derivative and a PET probe using the same.

BACKGROUND ART

In cancer diagnosis, it is important from the viewpoint of QOL to minimize pain and invasion in patients. Another key demand is to prevent healthy people from being unnecessarily disadvantaged by suspicion of having cancer. In recent years, minimally-invasive diagnostic imaging technology has advanced, and based on the fact that cancer cells take up a large amount of glucose, positron emission tomography (hereinafter referred to as "PET") using a $^{18}$F-labeled glucose analog $^{18}$F-fluorodeoxyglucose ($^{18}$F-FDG) is widely used. However, FDG has a disadvantage in that its uptake occurs in lesions other than cancer, such as inflammatory sites, leading to false positive results. Particularly, FDG uptake has been shown in normal tissues of the brain and inflammatory sites, and for this reason, the application of FDG is limited. Furthermore, the use of FDG in diabetic patients, who have difficulty in controlling their blood sugar levels, is also limited.

The present inventors previously discovered a novel amino acid transporter designated LAT1 (L-type amino acid transporter 1), which is responsible for amino acid uptake in cancer cells (Non Patent Literature 1). LAT1 is absent in normal cells in most tissues, but malignant transformation induces the expression of LAT1. Therefore, LAT1 can be used as a molecular marker of cancer diagnosis. In addition, the present inventors found an amino acid derivative that inhibits the cancer cell-specifically expressed amino acid transporter LAT1 and thereby suppresses cancer cell proliferation, and based on the findings, received a patent therefor (Patent Literature 1).

Furthermore, the present inventors conducted PET scans in lung cancer patients using $^{18}$F-labeled fluoro-α-methyltyrosine (hereinafter referred to as "FAMT"). FAMT is known to be intracellularly transported more dominantly via the cancer cell-specific amino acid transporter LAT1 than via an amino acid transporter designated LAT2 (L-type amino acid transporter 2), which is expressed in normal cells. The PET results showed that FAMT accumulated in cancer similarly to FDG and had a potential application for cancer diagnosis (Non Patent Literature 2). FAMT does not accumulate in inflammatory lesions and is highly selective for cancer, and therefore is a highly versatile PET probe that is applicable even to brain tumor, to which FDG is inapplicable.

However, the accumulation of FAMT is slightly less intense than that of FDG, and there is room for further improvement. Another problem is that the labeling of FAMT cannot be carried out with automated synthesizers commonly used in PET-installed institutions. Therefore, compounds for PET probes that can be labeled using automated synthesizers in the same manner as FDG are desired to be developed.

CITATION LIST

Patent Literature

Patent Literature 1: U.S. Pat. No. 4,705,756

Non Patent Literature

Non Patent Literature 1:
Kanai et al., J. Biol. Chem. 273: 23629, 1998
Non Patent Literature 2:
Kaira et al., Clin Cancer Res. 13: 6369-6378, 2007

SUMMARY OF INVENTION

Technical Problem

An object of the present invention is to find a compound which excels FAMT in terms of the tendency to accumulate intensively in cancer, the affinity for LAT1 and the selectivity for cancer, and can be labeled using an automated synthesizer in clinical settings, and to provide a highly versatile PET imaging agent.

Solution to Problem

The present invention includes the following to achieve the above-mentioned object.

(1) A compound having a structure represented by the general formula (I):

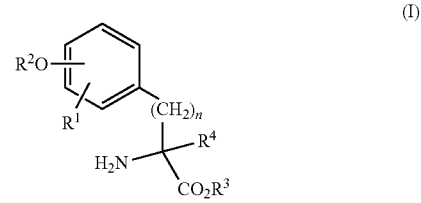

(wherein n is 0 or 1;
$R^1$ represents a hydrogen atom (only if n=0), a halogen atom, a C1-C6 alkyl group, a C1-C6 haloalkyl group, an optionally substituted amino group, an optionally substituted phenyl group, a C1-C6 alkylthio group, a C1-C6 alkoxy group, a C1-C6 haloalkoxy group or a C7-C12 aralkyloxy group;
$R^2$ represents —$(CH_2)_p$—$[O(CH_2)_q]_r$—X (wherein X is a halogen atom, p is an integer of 1 to 6, q is an integer of 1 to 4, and r is an integer of 0 to 4);
$R^3$ represents a hydrogen atom, a C1-C6 alkyl group, a C7-C16 aralkyl group or a C6-C14 aryl group; and
$R^4$ represents a hydrogen atom or a C1-C6 alkyl group), or a pharmaceutically acceptable salt thereof.

(2) The compound according to the above (1) or a pharmaceutically acceptable salt thereof, wherein the compound has an activity to specifically accumulate in cancer cells.

(3) The compound according to the above (1) or (2) or a pharmaceutically acceptable salt thereof, wherein X is a fluorine atom.

(4) The compound according to the above (3) or a pharmaceutically acceptable salt thereof, wherein the compound is 2-amino-3-(5-(2-fluoroethoxy)-2-iodophenyl) propanoic acid or 2-amino-3-(2-cyclopropyl-5-(2-fluoroethoxy)phenyl) propanoic acid.

(5) The compound according to the above (3) or a pharmaceutically acceptable salt thereof, wherein the compound is 2-amino-3-(2-bromo-5-(2-fluoroethoxy)phenyl) propanoic acid, 2-amino-3-(5-(4-fluorobutoxy)-2-iodophenyl)propanoic acid or 2-amino-3-(5-(2-(2-fluoroethoxy) ethoxy)-2-iodophenyl) propanoic acid.

(6) The compound according to any one of the above (1) to (5) or a pharmaceutically acceptable salt thereof, wherein the compound has a radioactive fluorine atom.
(7) The compound according to any one of the above (1) to (6) or a pharmaceutically acceptable salt thereof, wherein the compound having a structure represented by the general formula (I) is an optically active compound or a mixture of optically active compounds.
(8) A pharmaceutical composition comprising the compound according to anyone of the above (1) to (7) or a pharmaceutically acceptable salt thereof.
(9) The pharmaceutical composition according to the above (8), wherein the pharmaceutical composition is a positron emission tomography imaging agent for diagnostic use.
(10) The pharmaceutical composition according to the above (9) for use in detection of cancer tissues.
(11) The pharmaceutical composition according to the above (9) for evaluation of the malignancy of cancer.
(12) A precursor of the compound according to the above (6) or of a pharmaceutically acceptable salt thereof, the precursor being an optically active compound having a structure represented by the general formula (II):

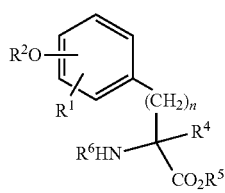

(wherein n is 0 or 1;
$R^1$ represents a hydrogen atom (only if n=0), a halogen atom, a C1-C6 alkyl group, a C1-C6 haloalkyl group, an optionally substituted amino group, an optionally substituted phenyl group, a C1-C6 alkylthio group, a C1-C6 alkoxy group, a C1-C6 haloalkoxy group or a C7-C12 aralkyloxy group;
$R^2$ represents —$(CH_2)_p$—[$O(CH_2)_q$]$_r$—Y (wherein Y is a leaving group, p is an integer of 1 to 6, q is an integer of 1 to 4, and r is an integer of 0 to 4);
$R^4$ represents a hydrogen atom or a C1-C6 alkyl group;
$R^5$ represents a hydrogen atom or a protecting group for a carboxyl group; and
$R^6$ represents a hydrogen atom or a protecting group for an amino group), or
a mixture of optically active compounds having the structure as defined above, or
a pharmaceutically acceptable salt thereof.
(13) A precursor of the compound according to the above (6) or of a pharmaceutically acceptable salt thereof, the precursor being an optically active compound having a structure represented by the general formula (III):

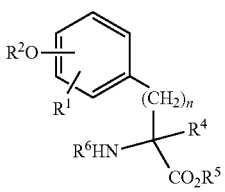

(wherein n is 0 or 1;
$R^1$ represents a hydrogen atom (only if n=0), a halogen atom, a C1-C6 alkyl group, a C1-C6 haloalkyl group, an optionally substituted amino group, an optionally substituted phenyl group, a C1-C6 alkylthio group, a C1-C6 alkoxy group, a C1-C6 haloalkoxy group or a C7-C12 aralkyloxy group;
$R^4$ represents a hydrogen atom or a C1-C6 alkyl group;
$R^5$ represents a hydrogen atom or a protecting group for a carboxyl group; and
$R^6$ represents a hydrogen atom or a protecting group for an amino group), or
a mixture of optically active compounds having the structure as defined above, or
a pharmaceutically acceptable salt thereof.

Advantageous Effects of Invention

The present invention can provide a compound which excels FAMT in terms of the tendency to accumulate intensively in cancer, the affinity for LAT1 and the selectivity for cancer, and can be labeled using an automated synthesizer in clinical settings. The compound is very useful as a highly versatile PET imaging agent.

DESCRIPTION OF EMBODIMENTS

Figure 1:
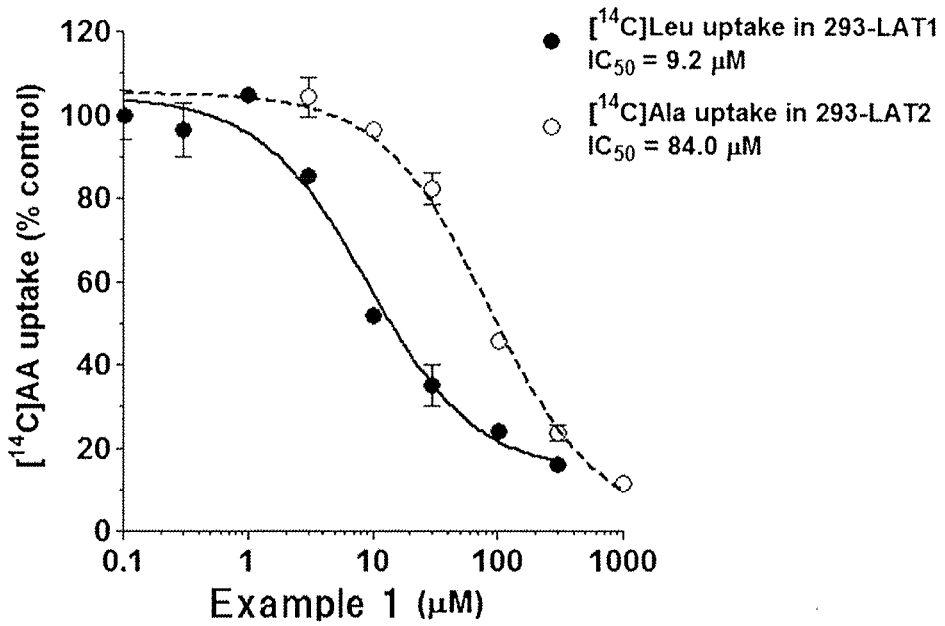
FIG. 1 shows the inhibitory effects of the compound of Example 1 on amino acid uptake in a human LAT1 stably expressing cell line and a human LAT2 stably expressing cell line.

The present invention provides a compound having a structure represented by the general formula (I):

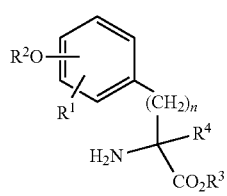

(wherein n is 0 or 1;
$R^1$ represents a hydrogen atom (only if n=0), a halogen atom, a C1-C6 alkyl group, a C1-C6 haloalkyl group, an optionally substituted amino group, an optionally substituted phenyl group, a C1-C6 alkylthio group, a C1-C6 alkoxy group, a C1-C6 haloalkoxy group or a C7-C12 aralkyloxy group;

$R^2$ represents $-(CH_2)_p-[O(CH_2)_q]_r-X$ (wherein X is a halogen atom, p is an integer of 1 to 6, q is an integer of 1 to 4, and r is an integer of 0 to 4);

$R^3$ represents a hydrogen atom, a C1-C6 alkyl group, a C7-C16 aralkyl group or a C6-C14 aryl group; and $R^4$ represents a hydrogen atom or a C1-C6 alkyl group), the compound being an optically active compound or a mixture of an optically active compounds such as a racemic mixture, or a pharmaceutically acceptable salt thereof.

The "halogen atom" represented by $R^1$ or $R^2$ may be a fluorine atom, a chlorine atom, a bromine atom or an iodine atom. X of $R^2$ is preferably a fluorine atom. X is more preferably a radioactive fluorine atom, and particularly preferably $^{18}F$.

The "C1-C6 alkyl group" represented by $R^1$, $R^3$ or $R^4$ may be in a straight, branched or cyclic form, and is for example, a methyl group, an ethyl group, a propyl group, an isopropyl group, a butyl group, a sec-butyl group, an isobutyl group, a tert-butyl group, a pentyl group, a hexyl group, a cyclopropyl group, a cyclobutyl group, a cyclopentyl group, a cyclohexyl group or the like. Preferred is a C1-C4 alkyl group. As used herein, for example, C1-C6 means that the number of carbon atoms is 1 to 6.

The "C1-C6 haloalkyl group" represented by $R^1$ may be in a straight, branched or cyclic form, and is for example, a chloromethyl group, a bromomethyl group, a fluoromethyl group, a trifluoromethyl group, a trichloromethyl group, a tribromomethyl group, a trichloroethyl group, a trifluoropropyl group, a pentafluoropropyl group or the like.

The "optionally substituted amino group" represented by $R^1$ may be a non-substituted amino group, a mono-substituted amino group, in which the amino group has one substituent, a di-substituted amino group, in which the amino group has two same or different substituents, or a 5- to 10-membered saturated aliphatic cyclic amino group in which two substituents on the amino group together with the nitrogen atom form a cyclic structure (in the aliphatic cyclic amino group, the ring atoms may include one or two oxygen or sulfur atoms). Examples of the substituent include a C1-C6 alkyl group, a C3-C8 cycloalkyl group, a C6-C10 aryl group and a 5- to 10-membered heteroaryl group. The specific examples include a methylamino group, an ethylamino group, a propylamino group, a dimethylamino group, a diethylamino group, an ethylmethylamino group, a methyl(phenyl)amino group, a pyrrolidinyl group, a piperidyl group, a piperazinyl group, a morpholinyl group and the like.

The "optionally substituted phenyl group" represented by $R^1$ may be a non-substituted phenyl group or a phenyl group optionally having 1 to 5 substituents. The substituent is not particularly limited and the examples include
(1) a halogen atom (a fluorine atom, a chlorine atom, a bromine atom, an iodine atom, etc.);
(2) a cyano group;
(3) C1-C6 alkoxy optionally having a halogen atom (methoxy, ethoxy, propoxy, isopropoxy, butoxy, isobutoxy, sec-butoxy, pentyloxy, hexyloxy, fluoromethoxy, etc.);
(4) alkylcarbonyl (acetyl, propionyl, etc.);
(5) alkylsulfonyl (methylsulfonyl, ethylsulfonyl, etc.);
(6) alkylenedioxy (methylenedioxy, ethylenedioxy, etc.);
(7) a C1-C6 alkyl group optionally having a halogen atom or hydroxy (methyl, ethyl, n-propyl, isopropyl, n-butyl, isobutyl, sec-butyl, tert-butyl, n-pentyl, sec-pentyl, isopentyl, neopentyl, n-hexyl, isohexyl, hydroxymethyl, etc.);
(8) mono-alkylcarbamoyl optionally substituted by hydroxy (methylcarbamoyl, ethylcarbamoyl, 2-hydroxyethylcarbamoyl, etc.);
(9) alkylcarbonyloxy (acetoxy etc.); and
(10) a 5- to 10-membered aromatic heterocyclic group which is optionally substituted by 1 to 3 alkyl groups and contains a carbon atom(s) and 1 to 4 heteroatoms of one or two kinds which are selected from a nitrogen atom, a sulfur atom and an oxygen atom (a 5- or 6-membered aromatic heterocyclic group such as 1,3,4-oxadiazolyl)).

The "C1-C6 alkylthio group" represented by $R^1$ may be in a straight, branched or cyclic form, and is for example, a methylthio group, an ethylthio group, a propylthio group, an isopropylthio group, a butylthio group, an isobutylthio group, a tert-butylthio group, a pentylthio group, a hexylthio group, a cyclohexylthio group or the like.

The "C1-C6 alkoxy group" represented by $R^1$ may be in a straight, branched or cyclic form, and is for example, a methoxy group, an ethoxy group, a propoxy group, an isopropoxy group, a butoxy group, an isobutoxy group, a tert-butoxy group, a pentyloxy group, a hexyloxy group, a cyclohexyloxy group or the like.

The "C1-C6 haloalkoxy group" represented by $R^1$ may be in a straight, branched or cyclic form, and is for example, a fluoromethoxy group, a difluoromethoxy group, trifluoromethoxy group, a 2,2,2-trifluoroethoxy group, a perfluoroethoxy group, a perfluoropropoxy group, a perfluorobutoxy group, a perfluoropentyloxy group, a perfluorohexyloxy group or the like.

The "C7-C16 aralkyloxy group" represented by $R^1$ is, for example, a benzyloxy group, a phenylethoxy group, a phenylpropoxy group, a phenylbutoxy group, a phenylpentyloxy group, a naphthylmethoxy group or the like.

The "$-(CH_2)_p-[O(CH_2)_q]_r-X$ group" represented by $R^2$ is, for example, a fluoromethyl group, a fluoroethyl group, a fluoropropyl group, a fluorobutyl group, a fluoromethoxymethyl group, a fluoroethoxyethyl group, a fluoroethoxymethyl group, a fluoromethoxy methoxymethyl group, a fluoroethoxy ethoxyethyl group, a fluoroethoxy ethoxymethyl group or the like.

The "C7-C16 aralkyl group" represented by $R^3$ is, for example, a benzyl group, a phenylethyl group, a phenylpropyl group, a naphthylmethyl group, a naphthylethyl group, a naphthylpropyl group or the like.

The "C6-C14 aryl group" represented by $R^3$ is, for example, a phenyl group, a tolyl group, a xylyl group, a cumenyl group, a mesityl group, a naphthyl group, a biphenylyl group or the like.

Examples of the compound of the present invention represented by the general formula (I) include the following compounds (1) to (70).
(1) 2-amino-3-(2-cyclopropyl-5-(2-fluoroethoxy)phenyl) propanoic acid
(2) 2-amino-3-(2-cyclopropyl-5-(3-fluoropropoxy)phenyl) propanoic acid
(3) 2-amino-3-(2-cyclopropyl-5-(2-(2-fluoroethoxy)ethoxy) phenyl) propanoic acid
(4) 2-amino-3-(4-(2-fluoroethoxy)-[1,1'-biphenyl]-2-yl)propanoic acid
(5) 2-amino-3-(5-(3-fluoropropoxy)-2-iodophenyl)propanoic acid
(6) 2-amino-3-(5-(2-(2-fluoroethoxy)ethoxy)-2-iodophenyl) propanoic acid
(7) 2-amino-3-(3-(2-fluoroethoxy)-4-iodophenyl)propanoic acid
(8) 2-amino-3-(6-(2-fluoroethoxy)-[1,1'-biphenyl]-3-yl)propanoic acid (9) 2-amino-3-(4-(2-(2-fluoroethoxy)ethoxy)-3-iodophenyl)propanoic acid
(10) 2-amino-3-(3-(2-(2-fluoroethoxy)ethoxy)-4-iodophenyl)propanoic acid
(11) 2-amino-3-(6-(2-(2-fluoroethoxy)ethoxy)-[1,1'-biphenyl]-3-yl) propanoic acid
(12) 2-amino-3-(2-bromo-5-(2-fluoroethoxy)phenyl)propanoic acid
(13) 2-amino-3-(5-(4-fluorobutoxy)-2-iodophenyl)propanoic acid
(14) 2-amino-3-(5-(2-(2-(2-fluoroethoxy)ethoxy)ethoxy)-2-iodophenyl) propanoic acid
(15) 2-amino-3-(2-bromo-5-(2-(2-fluoroethoxy)ethoxy)phenyl)propanoic acid
(16) 2-amino-3-(5-(2-fluoroethoxy)-2-iodophenyl)propanoic acid
(17) 2-amino-3-(4-(2-fluoroethoxy)-3-iodophenyl)propanoic acid
(18) 2-amino-3-(5-(2-fluoroethoxy)-2-hexylphenyl)propanoic acid
(19) 2-amino-3-(5-(2-fluoroethoxy)-2-isopropylphenyl)propanoic acid
(20) 2-amino-3-(2-(tert-butyl)-5-(2-fluoroethoxy)phenyl) propanoic acid
(21) 2-amino-3-(2-cyclobutyl-5-(2-fluoroethoxy)phenyl) propanoic acid
(22) 2-amino-3-(2-cyclopentyl-5-(2-fluoroethoxy)phenyl) propanoic acid
(23) 2-amino-3-(2-cyclohexyl-5-(2-fluoroethoxy)phenyl) propanoic acid
(24) 2-amino-3-(2-fluoro-5-(2-fluoroethoxy)phenyl)propanoic acid
(25) 2-amino-3-(5-(2-fluoroethoxy)-2-(trifluoromethyl)phenyl)propanoic acid
(26) 2-amino-3-(5-(2-fluoroethoxy)-2-(fluoromethyl)phenyl)propanoic acid
(27) 2-amino-3-(2-(dimethylamino)-5-(2-fluoroethoxy)phenyl)propanoic acid
(28) 2-amino-3-(5-(2-fluoroethoxy)-2-(methylamino)phenyl)propanoic acid
(29) 2-amino-3-(2-(aziridin-1-yl)-5-(2-fluoroethoxy)phenyl)propanoic acid
(30) 2-amino-3-(5-(2-fluoroethoxy)-2-(pyrrolidin-1-yl)phenyl)propanoic acid
(31) 2-amino-3-(2-(azetidin-1-yl)-5-(2-fluoroethoxy)phenyl)propanoic acid
(32) 2-amino-3-(5-(2-fluoroethoxy)-2-(piperidin-1-yl)phenyl)propanoic acid
(33) 2-amino-3-(2-(ethylthio)-5-(2-fluoroethoxy)phenyl) propanoic acid
(34) 2-amino-3-(5-(2-fluoroethoxy)-2-(pentyloxy)phenyl) propanoic acid
(35) 2-amino-3-(5-(2-fluoroethoxy)-2-isopropoxyphenyl) propanoic acid
(36) 2-amino-3-(2-cyclobutoxy-5-(2-fluoroethoxy)phenyl) propanoic acid
(37) 2-amino-3-(2-(benzyloxy)-5-(2-fluoroethoxy)phenyl) propanoic acid
(38) 2-amino-3-(2-cyclopropyl-5-(2-fluoroethoxy)phenyl)-2-methyl propanoic acid
(39) 2-amino-3-(5-(2-fluoroethoxy)-2-iodophenyl)-2-methylpropanoic acid
(40) 2-amino-3-(2-cyclopropyl-5-(2-(2-fluoroethoxy)ethoxy)phenyl-2-methylpropanoic acid
(41) 2-amino-3-(4-(2-fluoroethoxy)-[1,1'-biphenyl]-2-yl)-2-methylpropanoic acid
(42) 2-amino-3-(5-(2-(2-fluoroethoxy)ethoxy)-2-iodophenyl)-2-methylpropanoic acid
(43) 2-amino-3-(3-(2-fluoroethoxy)-4-iodophenyl)-2-methylpropanoic acid
(44) 2-amino-3-(5-(2-fluoroethoxy)-2-(pentyloxy)phenyl)-2-methyl propanoic acid
(45) 2-amino-3-(2-cyclohexyl-5-(2-fluoroethoxy)phenyl)-2-methylpropanoic acid
(46) 2-amino 3 (2-fluoro-5-(2-fluoroethoxy)phenyl)-2-methylpropanoic acid
(47) 2-amino-3-(5-(2-fluoroethoxy)-2-(trifluoromethyl)phenyl)-2-methylpropanoic acid
(48) 2-amino-3-(2-(tert-butyl)-5-(2-fluoroethoxy)phenyl)-2-methylpropanoic acid
(49) 2-amino-3-(2-(dimethylamino)-5-(2-fluoroethoxy)phenyl)-2-methylpropanoic acid
(50) 2-amino-3-(5-(2-fluoroethoxy)-2-(methylthio)phenyl)-2-methylpropanoic acid
(51) 2-amino-3-(5-(2-fluoroethoxy)-2-(pyrrolidin-1-yl)phenyl)-2-methylpropanoic acid
(52) 2-amino-3-(2-(benzyloxy)-5-(2-fluoroethoxy)phenyl)-2-methylpropanoic acid
(53) ethyl 2-amino-3-(2-cyclopropyl-5-(2-fluoroethoxy)phenyl)propanoate
(54) ethyl 2-amino-3-(5-(2-fluoroethoxy)-2-iodophenyl) propanoate
(55) ethyl 2-amino-3-(2-cyclopropyl-5-(2-fluoroethoxy)phenyl)-2-methyl propanoate
(56) ethyl 2-amino-3-(5-(2-fluoroethoxy)-2-iodophenyl)-2-methylpropanoate
(57) benzyl 2-amino-3-(2-cyclopropyl-5-(2-fluoroethoxy)phenyl)propanoate
(58) benzyl 2-amino-3-(5-(2-fluoroethoxy)-2-iodophenyl) propanoate
(59) benzyl 2-amino-3-(2-cyclopropyl-5-(2-fluoroethoxy)phenyl)-2-methyl propanoate
(60) benzyl 2-amino-3-(5-(2-fluoroethoxy)-2-iodophenyl)-2-methylpropanoate
(61) 2-amino-2-(3-cyclopropyl-4-(2-fluoroethoxy)phenyl) acetic acid
(62) 2-amino-2-(4-(2-fluoroethoxy)-3-iodophenyl)acetic acid
(63) 2-amino-2-(2-cyclopropyl-5-(2-fluoroethoxy)phenyl) acetic acid
(64) 2-amino-2-(5-(2-fluoroethoxy)-2-iodophenyl)acetic acid
(65) benzyl 2-amino-2-(2-cyclopropyl-5-(2-fluoroethoxy) phenyl)acetate
(66) benzyl 2-amino-2-(5-(2-fluoroethoxy)-2-iodophenyl) acetate
(67) ethyl 2-amino-2-(2-cyclopropyl-5-(2-fluoroethoxy) phenyl)acetate
(68) ethyl 2-amino-2-(5-(2-fluoroethoxy)-2-iodophenyl)acetate
(69) 2-amino-2-(4-(2-fluoroethoxy)phenyl)acetic acid
(70) 2-amino-2-(3-(2-fluoroethoxy)phenyl)acetic acid Among these compounds, preferred are (16) 2-amino-3-(5-(2-fluoroethoxy)-2-iodophenyl)propanoic acid, (1) 2-amino-3-(2-cyclopropyl-5-(2-fluoroethoxy)phenyl)propanoic acid, (12) 2-amino-3-(2-bromo-5-(2-fluoroethoxy)phenyl)propanoic acid, (13) 2-amino-3-(5-(4-fluorobutoxy)-2-iodophenyl) propanoic acid, (6) 2-amino-3-(5-(2-(2-fluoroethoxy)ethoxy)-2-iodophenyl) propanoic acid, etc.

The structural formulae of the above compounds (1) to (70) are shown in Tables 1 to 3.
TABLE 1
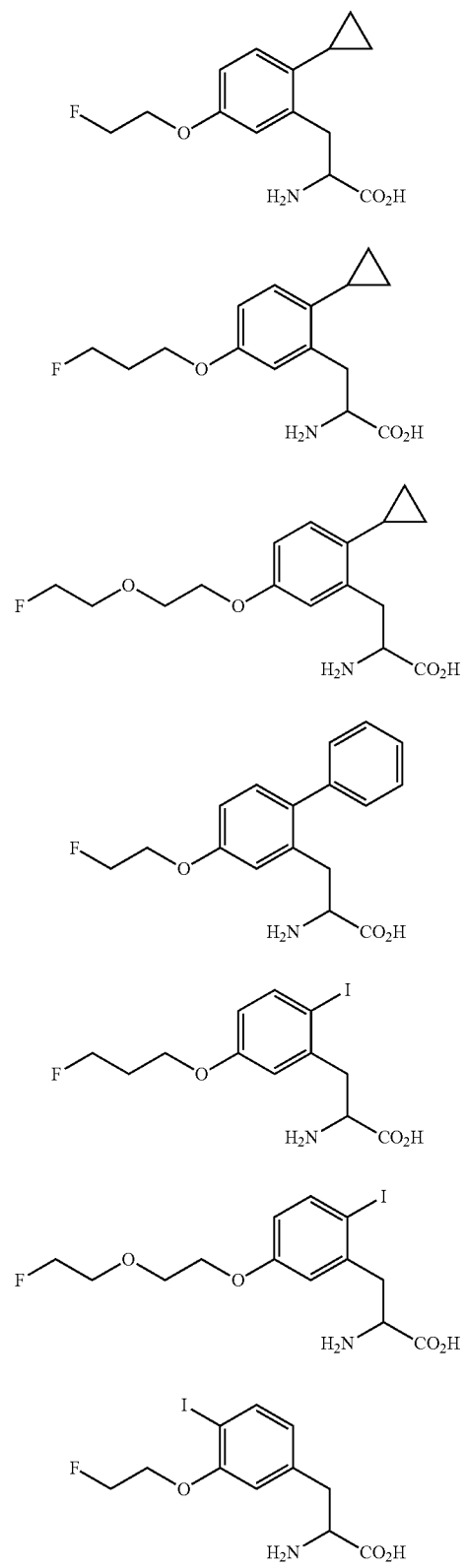
TABLE 1-continued
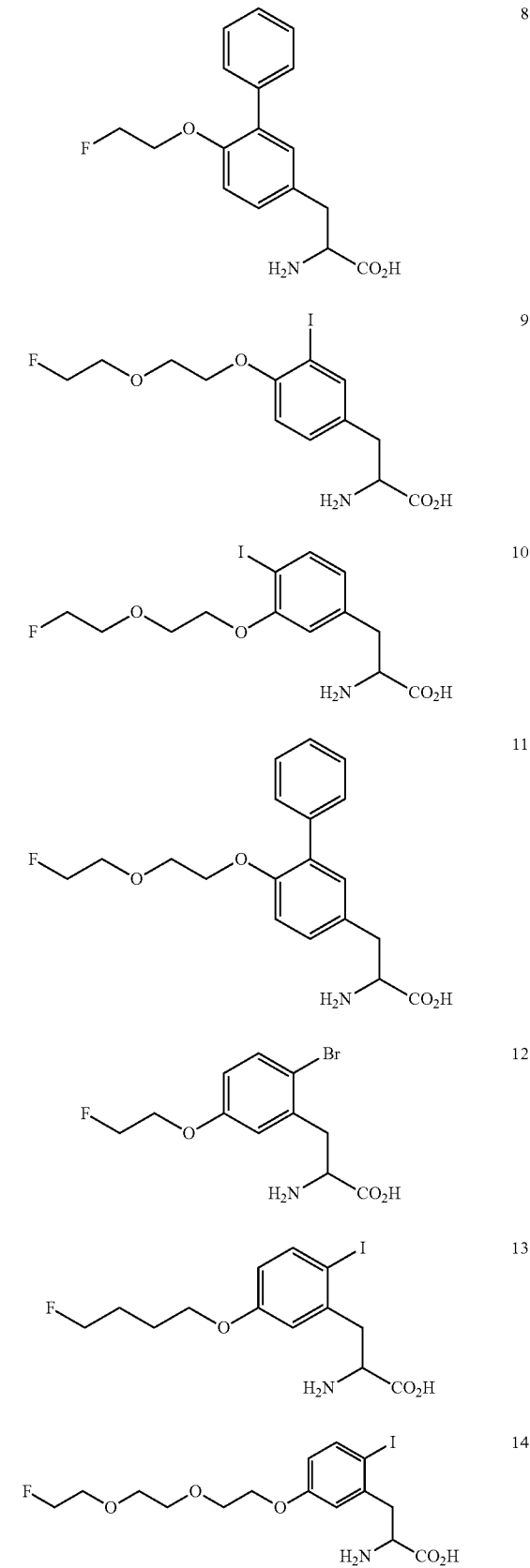

TABLE 1-continued
15 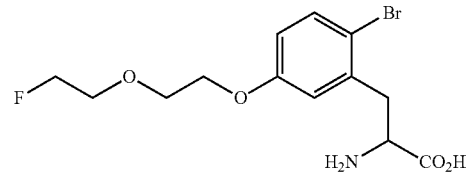 [SMILES: NC(Cc1cc(OCCOCCF)ccc1I)C(=O)O]
16 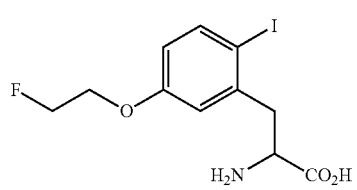 [SMILES: NC(Cc1cc(OCCF)ccc1I)C(=O)O]
17 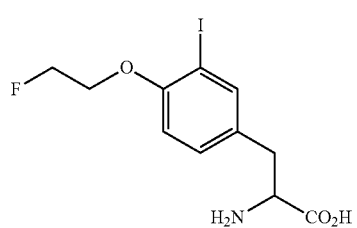 [SMILES: NC(Cc1ccc(OCCF)c(I)c1)C(=O)O]
18 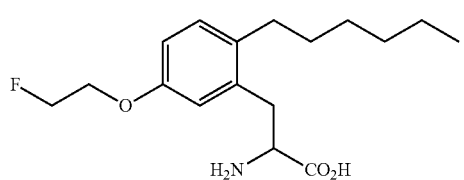 [SMILES: CCCCCCc1ccc(OCCF)cc1CC(N)C(=O)O]
19 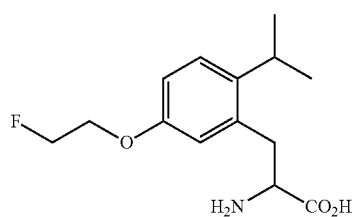 [SMILES: CC(C)c1ccc(OCCF)cc1CC(N)C(=O)O]
20 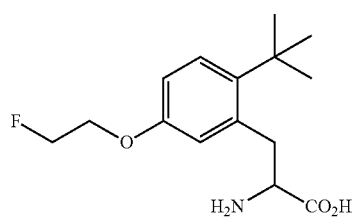 [SMILES: CC(C)(C)c1ccc(OCCF)cc1CC(N)C(=O)O]
21 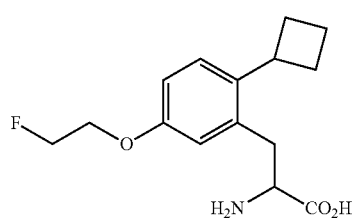
TABLE 1-continued
22 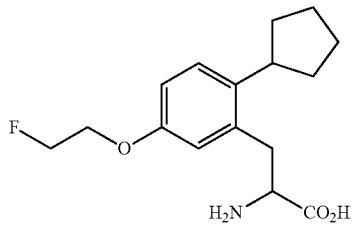 [SMILES: NC(Cc1cc(OCCF)ccc1N1CCCC1)C(=O)O]
23 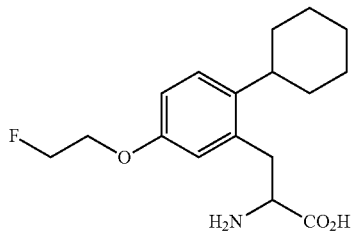 [SMILES: NC(Cc1cc(OCCF)ccc1N1CCCCC1)C(=O)O]
24 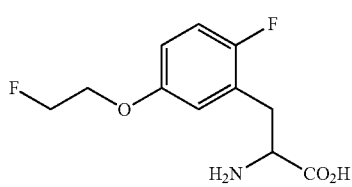
25 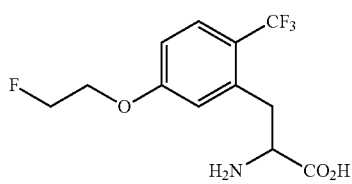 [SMILES: NC(Cc1cc(OCCF)ccc1I)C(=O)O]
26 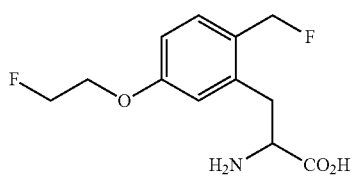
27 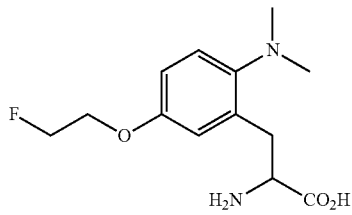
28 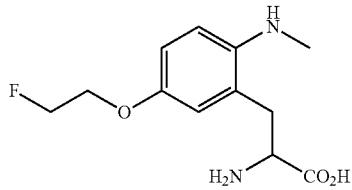

TABLE 2
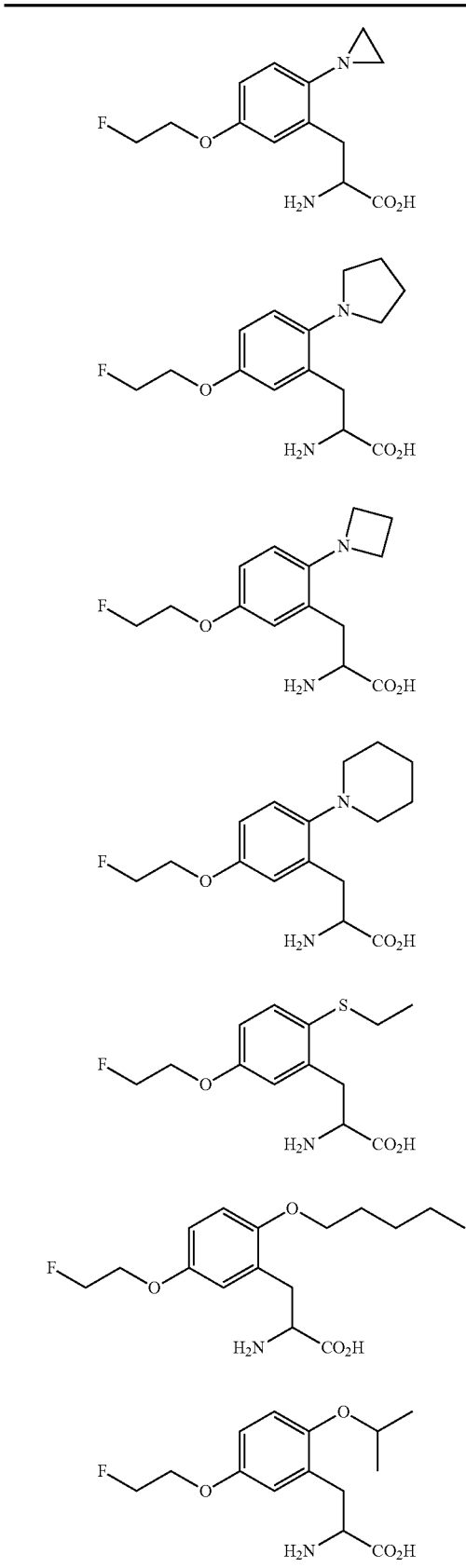
TABLE 2-continued
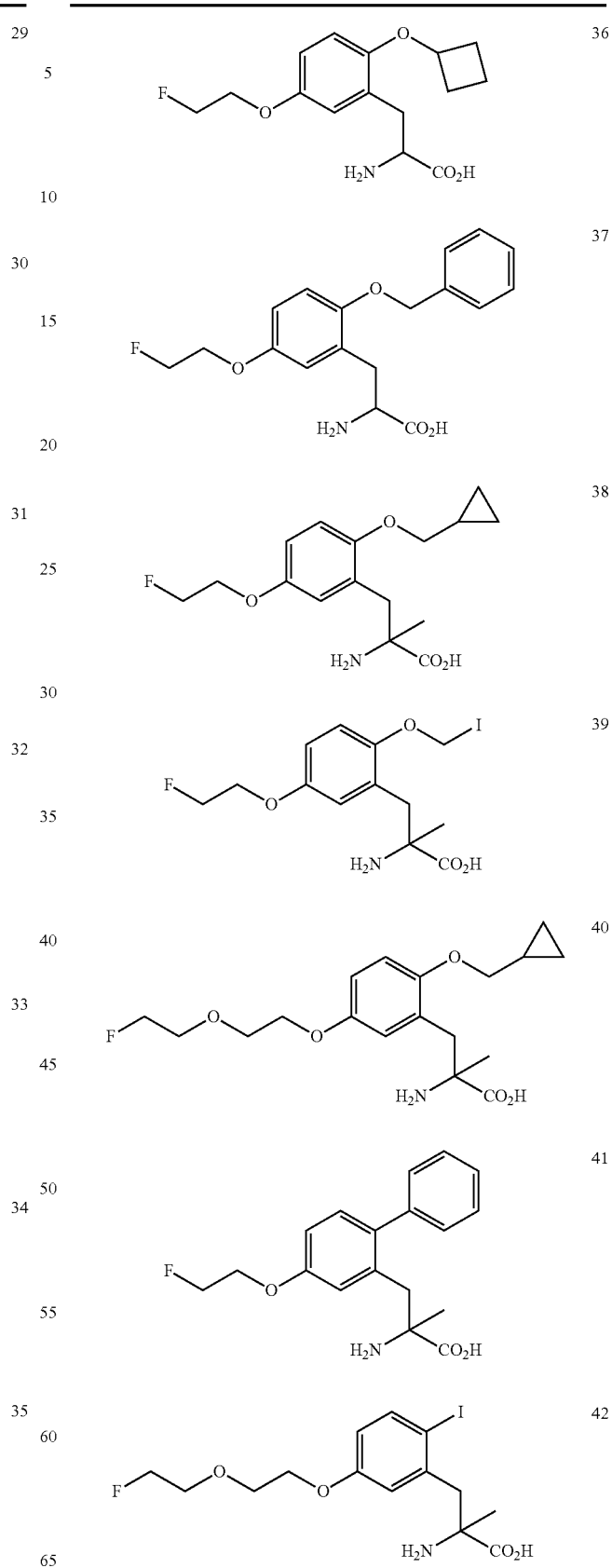

TABLE 2-continued
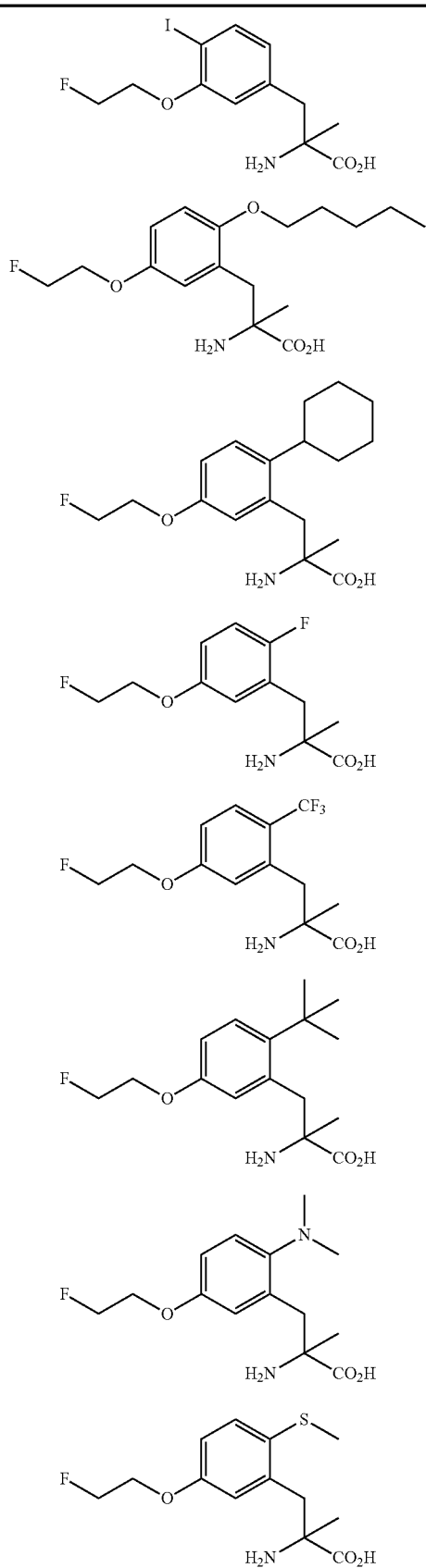
TABLE 2-continued
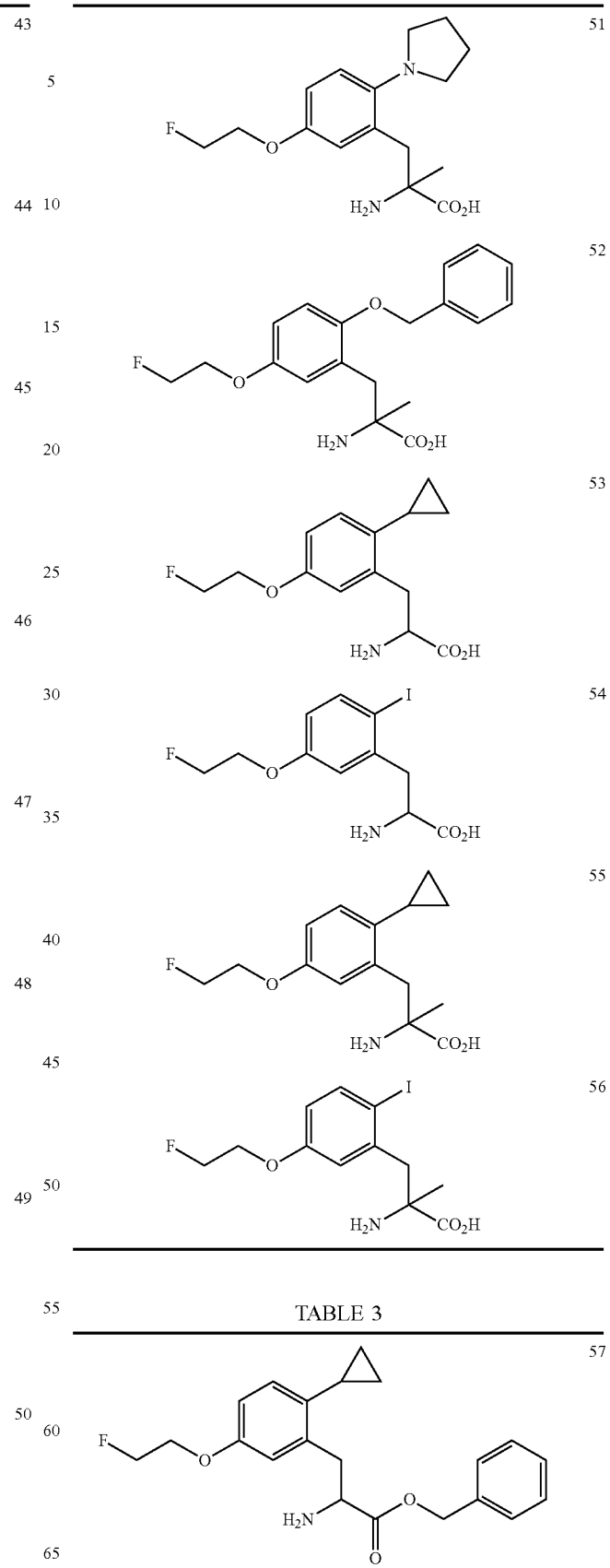
TABLE 3

TABLE 3-continued
| | |
|---|---|
| 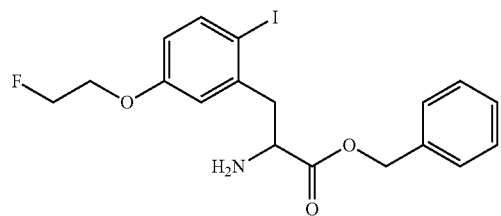 [SMILES: NC(Cc1cc(OCCF)ccc1I)C(=O)OCc1ccccc1] | 58 |
| 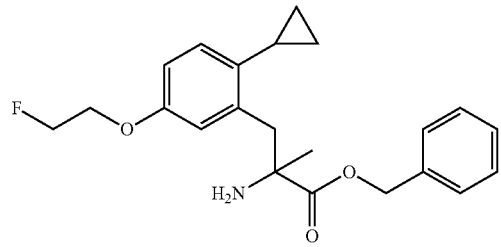 [SMILES: CC(N)(Cc1cc(OCCF)ccc1C1CC1)C(=O)OCc1ccccc1] | 59 |
| 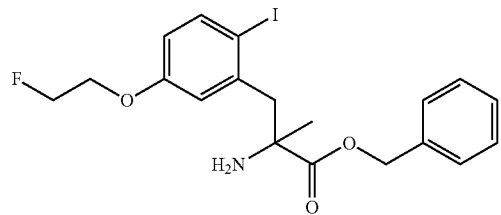 [SMILES: CC(N)(Cc1cc(OCCF)ccc1I)C(=O)OCc1ccccc1] | 60 |
| 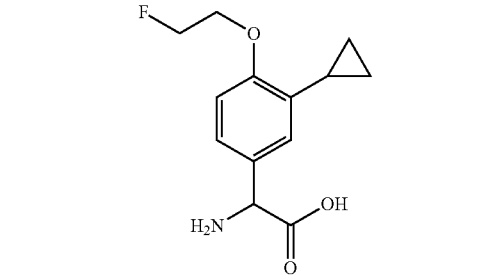 [SMILES: NC(C(=O)O)c1ccc(OCCF)c(C2CC2)c1] | 61 |
| 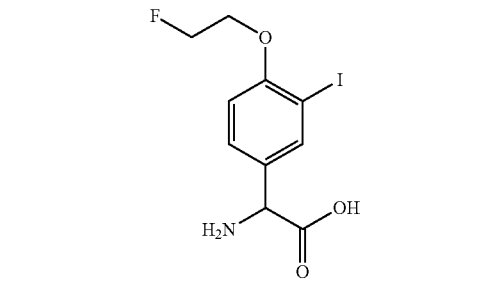 | 62 |
| 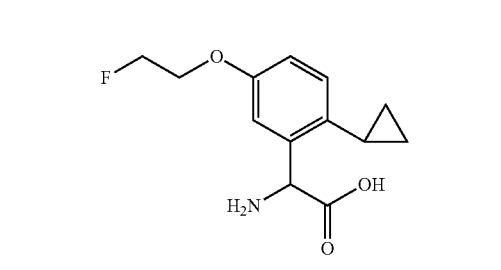 [SMILES: NC(C(=O)O)c1cc(OCCF)ccc1C1CC1] | 63 |
TABLE 3-continued
| | |
|---|---|
| 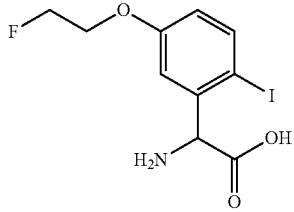 [SMILES: NC(C(=O)O)c1cc(OCCF)ccc1I] | 64 |
| 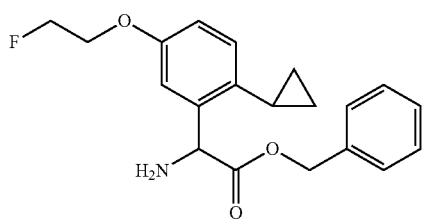 [SMILES: NC(C(=O)OCc1ccccc1)c1cc(OCCF)ccc1C1CC1] | 65 |
| 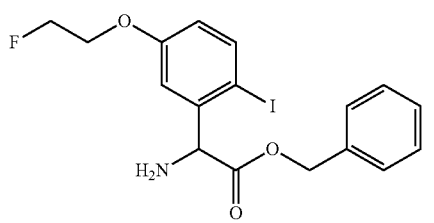 [SMILES: NC(C(=O)OCc1ccccc1)c1cc(OCCF)ccc1I] | 66 |
| 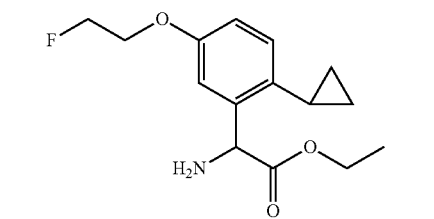 [SMILES: CCOC(=O)C(N)c1cc(OCCF)ccc1C1CC1] | 67 |
| 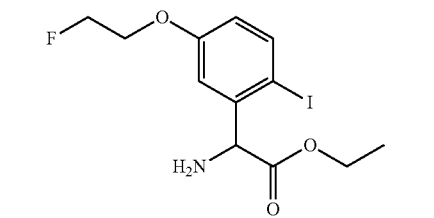 [SMILES: CCOC(=O)C(N)c1cc(OCCF)ccc1I] | 68 |
| 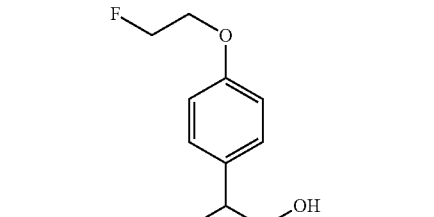 | 69 |
| 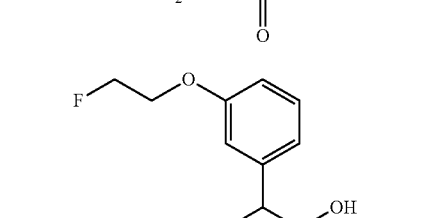 | 70 |

Examples of the "pharmaceutically acceptable salt" include salts of alkali metals (for example, potassium, sodium, lithium, etc.), salts of alkaline earth metals (for example, calcium, magnesium, etc.), ammonium salts (for example, a tetramethylammonium salt, a tetrabutylammonium salt, etc.), salts of organic amines (for example, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), and acid addition salts (for example, inorganic acid salts, such as hydrochlorides, hydrobromides, hydriodides, sulfates, phosphates and nitrates; and organic acid salts, such as acetates, trifluoroacetates, lactates, tartrates, oxalates, fumarates, maleates, benzoates, citrates, methanesulfonates, ethanesulfonates, benzenesulfonates, toluenesulfonates, isethionates, glucuronates and gluconates).

Hereinafter, an optically active compound having a structure represented by the general formula (I) of the present invention; any mixture of optically active compounds having the structure as defined above, such as a racemic mixture; or a pharmaceutically acceptable salt thereof is referred to as "the compound of the present invention".

The compound of the present invention preferably has a radioactive fluorine atom. The position of the radioactive fluorine atom is not particularly limited, but X of $R^2$ in the general formula (I) is preferred. The radioactive fluorine atom is preferably $^{18}F$.

The compound of the present invention preferably has an activity to specifically accumulate in cancer cells (a tendency to be incorporated specifically into cancer cells and accumulate therein). The method for confirming whether the compound of the present invention has such an activity is not particularly limited, and known methods for evaluating compounds for the activity to specifically accumulate in cancer cells can be selected as appropriate. For example, an amino acid uptake inhibition test using a human LAT1 stably expressing cell line and a human LAT2 stably expressing cell line (Khunweeraphong et al. J Pharmacol Sci. 2012 Aug. 18; 119(4): 368-80. Epub 2012 Jul. 31) can be used (see Examples 1 and 2). In this test, when the presence of a compound results in higher percentage of inhibition of amino acid uptake in the human LAT1 stably expressing cell line than in the human LAT2 stably expressing cell line, the compound can be selected as a compound having an activity to specifically accumulate in cancer cells. As for selection criteria, it is preferable to select a compound having higher activity to specifically accumulate in cancer cells than FAMT as a control. To be more specific, it is preferable to select a compound that surpasses FAMT in the percentage of inhibition of amino acid uptake in the human LAT1 stably expressing cell line, for example. Alternatively, it is preferable to select a compound that has higher selectivity for cancer cells than FAMT with the proviso that the selectivity is determined by the following formula:

Cancer cell selectivity=Amino acid uptake activity in human LAT2 stably expressing cell line/Amino acid uptake activity in human LAT1 stably expressing cell line    (Formula)

In addition, the present invention provides a precursor of the compound of the present invention. The precursor is preferably an optically active compound having a structure represented by the general formula (II) or (III); a mixture of optically active compounds having the structure as defined above; or a pharmaceutically acceptable salt thereof.

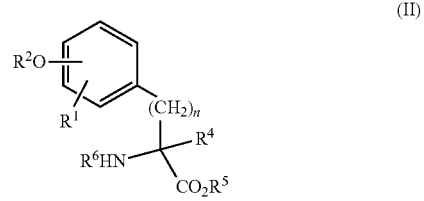

(II)

In the formula, n is 0 or 1;
$R^1$ represents a hydrogen atom (only if n=0), a halogen atom, a C1-C6 alkyl group, a C1-C6 haloalkyl group, an optionally substituted amino group, an optionally substituted phenyl group, a C1-C6 alkylthio group, a C1-C6 alkoxy group, a C1-C6 haloalkoxy group or a C7-C12 aralkyloxy group;
$R^2$ represents —$(CH_2)_p$—$[O(CH_2)_q]_r$—Y (wherein Y is a leaving group, p is an integer of 1 to 6, q is an integer of 1 to 4, and r is an integer of 0 to 4);
$R^4$ represents a hydrogen atom or a C1-C6 alkyl group;
$R^5$ represents a hydrogen atom or a protecting group for a carboxyl group; and
$R^6$ represents a hydrogen atom or a protecting group for an amino group.

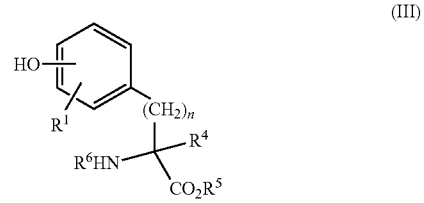

(III)

In the formula, n is 0 or 1;
$R^1$ represents a hydrogen atom (only if n=0), a halogen atom, a C1-C6 alkyl group, a C1-C6 haloalkyl group, an optionally substituted amino group, an optionally substituted phenyl group, a C1-C6 alkylthio group, a C1-C6 alkoxy group, a C1-C6 haloalkoxy group or a C7-C12 aralkyloxy group;
$R^4$ represents a hydrogen atom or a C1-C6 alkyl group;
$R^5$ represents a hydrogen atom or a protecting group for a carboxyl group; and
$R^6$ represents a hydrogen atom or a protecting group for an amino group.

$R^1$ and $R^4$ are as defined for the general formula (I).

$R^5$ is not particularly limited as long as it is a commonly used protecting group for a carboxyl group. For example, $R^5$ is a methyl group, an ethyl group, a propyl group, an isopropyl group, a butyl group, an isobutyl group, a sec-butyl group, a tert-butyl group, a hexyl group, a bromo-tert-butyl group, a trichloroethyl group, a benzyl group, a p-nitrobenzyl group, an o-nitrobenzyl group, a p-methoxybenzyl group, a diphenylmethyl group, a trityl group, a p-tert-butylbenzyl group, an acetoxymethyl group, a propionyloxymethyl group, a butyryloxymethyl group, an isobutyryloxymethyl group, a valeryloxymethyl group, a pivaloyloxymethyl group, an acetoxyethyl group, an acetoxypropyl group, an acetoxybutyl group, a propionyloxyethyl group, a propionyloxypropyl group, a butyryloxyethyl group, an isobutyryloxyethyl group, a pivaloyloxyethyl group, a hexanoyloxyethyl group, an ethylbutyryloxymethyl group, a dimethylbutyryloxymethyl group, a pentanoyloxyethyl group, a methoxycarbonyloxymethyl group, an ethoxycarbonyloxymethyl group, a propoxycarbonyloxymethyl group, a tert-butoxycarbonyloxymethyl group, a methoxycarbonyloxyethyl group, an ethoxycarbonyloxyethyl group, an isopropoxycarbonyloxyethyl group, a tert-butyldimethylsilyl group, a trimethylsilyl group, a methoxymethyl group, an ethoxymethyl group, a propoxymethyl group, an isopropoxymethyl group, a (2-methylthio)-ethyl group, a 3-methyl-2-butenyl group, a 5-indanyl group, a 3-phthalidyl group or the like. Preferred are a tert-butyl group, a benzyl group, a p-methoxybenzyl group, a diphenylmethyl group and a trityl group.

$R^6$ is not particularly limited as long as it is a commonly used protecting group for an amino group. $R^6$ is, for example, a formyl group, a phenylcarbonyl group, a methoxycarbonyl group, an ethoxycarbonyl group, a tert-butoxycarbonyl group, a phenyloxycarbonyl group, a 9-fluorenylmethyloxycarbonyl group, an adamantyloxycarbonyl group, a benzyloxycarbonyl group, a benzylcarbonyl group, a benzyl group, a benzhydryl group, a trityl group, a phthaloyl group or the like. Preferred are a tert-butoxycarbonyl group, a trityl group and a benzyloxycarbonyl group.

Y is not particularly limited as long as it is a commonly used leaving group. Y is, for example, iodine, an alkylsulfonyloxy group, an arylsulfonyloxy group or the like, and specific examples of the alkylsulfonyloxy or arylsulfonyloxy group include a mesyloxy group, a tosyloxy group, a trifluoromethylsulfonyloxy group, a nona-fluorobutylsulfonyloxy group, a (4-bromophenyl)sulfonyloxy group, a (4-nitrophenyl)sulfonyloxy group, a (2-nitrophenyl)sulfonyloxy group, a (4-isopropylphenyl)sulfonyloxy group, a (2,4,6-triisopropylphenyl)sulfonyloxy group, a (2,4,6-trimethylphenyl)sulfonyloxy group, a (4-tert-butylphenyl)sulfonyloxy group and a (4-methoxyphenyl)sulfonyloxy group. Preferred are a mesyloxy group, a tosyloxy group and a trifluoromethylsulfonyloxy group.

The method for producing the compound of the present invention is not particularly limited, and for example, the compound of the present invention can be produced in accordance with the synthesis method described in Example 1. The method for producing the radioactive fluorine-labeled compound of the present invention from the precursor of the present invention is, for example, as follows. The precursor represented by the general formula (II) or (III) is subjected to a reaction with an appropriate radiolabeling agent containing radioactive fluorine, followed by, as needed, deprotection and purification by HPLC etc. to give a desired compound. Preferable examples of the radiolabeling agent containing radioactive fluorine include 4,7,13,16,21,24-hexoxa-1,10-diazabicyclo[8,8,8]-hexacosane $K^{18}F$ (namely a crown ether salt, Kryptofix $K^{18}F$) $K^{18}F$, $H^{18}F$, $KH^{18}F_2$, $Cs^{18}F$ and $Na^{18}F$; and a tetraalkylammonium salt of $^{18}F$, for example, tetrabutylammonium fluoride. The radioactive fluorine can be obtained by a known method, for example, proton irradiation of $H_2^{18}O$ concentrated water. The resulting mixture of $H_2^{18}O$ concentrated water and radioactive fluorine is, for example loaded onto an anion exchange column, which traps the radioactive fluorine by adsorption, and the radioactive fluorine is separated from the $H_2^{18}O$ concentrated water. Afterwards, in one example, the trapped radioactive fluorine is eluted with a potassium carbonate solution, a phase transfer catalyst is added to the eluate, which is used for use in a labeling reaction. Alternatively, the radioactive fluorine may be eluted with a tetra-N-butylammonium hydrogen carbonate solution and obtained in the eluate, which is directly used for a labeling reaction. Other methods can also be employed.

The precursor represented by the general formula (II) or (III) can be easily produced by a known method or a method known per se, or in accordance with the synthesis method described in Example 1.

For example, radioactive fluorine-labeled 2-amino-3-(5-(2-fluoroethoxy)-2-iodophenyl)propanoic acid (compound 16 in Table 1) can be synthesized by the scheme shown below. Other radioactive fluorine-labeled compounds of the present invention can also be synthesized in accordance with this scheme. Here, 6 in the following scheme stands for compound 6 in the synthesis scheme of Example 1.

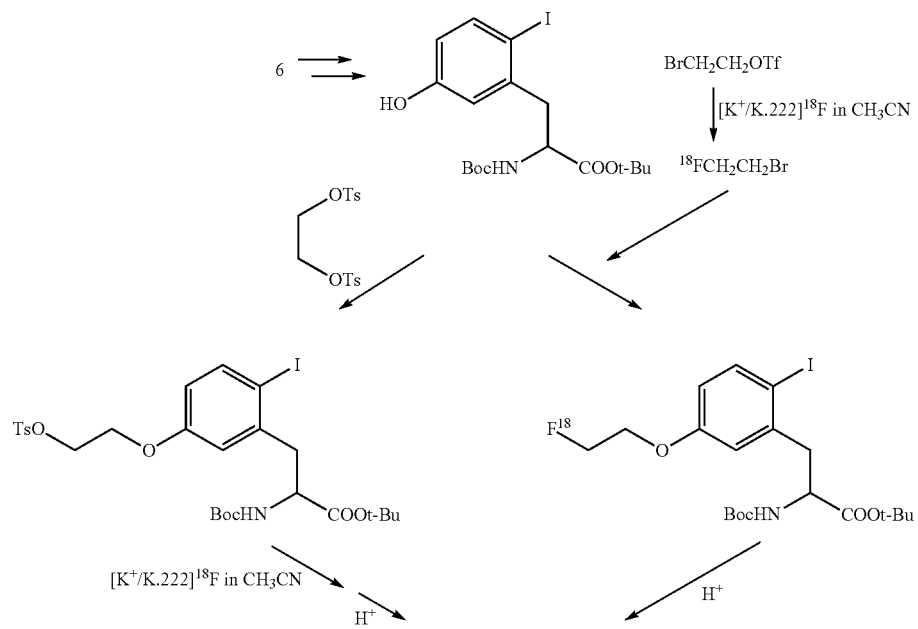

-continued

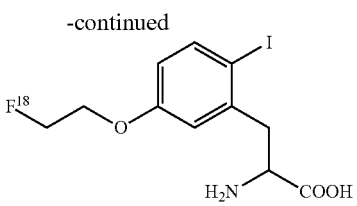

Since the compound of the present invention has high activity to specifically accumulate in cancer cells, it is useful for a pharmaceutical composition for cancer diagnosis. The pharmaceutical composition of the present invention is preferably a PET imaging agent for diagnostic use.

The pharmaceutical composition of the present invention can be formulated by blending the compound of the present invention, a pharmaceutically acceptable carrier and an additive as appropriate. The PET imaging agent for diagnostic use is preferably a liquid preparation, and particularly preferably an injection. The administration to a subject may be local or systemic administration, but preferably systemic administration. The administration route is not particularly limited, but is preferably intravenous injection or infusion. Injections can be prepared by a method known in the art. For preparation of a solution for injection, for example the compound of the present invention is dissolved in an appropriate liquid carrier (water for injection, physiological saline, Ringer's solution or the like), the resulting solution is sterilized with a filter or the like, and the filtrate is packed into appropriate containers such as vials and ampoules. For dissolution of the compound of the present invention, appropriate solubilizers, for example, alcohols, polyalcohols, non-ionic surfactants or the like may be used. As another additive, saccharides or sugar alcohols may also be used. Sugar alcohols are preferably used and the examples include erythritol, xylitol, sorbitol and mannitol. The prepared solution may be freeze-dried for reconstitution in an appropriate liquid carrier just before use. For preparation of a suspension for injection, for example, the compound of the present invention is sterilized with ethylene oxide or the like, and suspended in a sterilized liquid carrier.

The composition of the present invention may be administered to any subject without particular limitation and the examples of the subject include humans and other mammals (rats, mice, rabbits, sheep, pigs, cows, cats, dogs, monkeys, etc.).

The dose can be determined as appropriate according to the conditions including the body weight, age and sex of the administration subject, and the kind of the PET scanner used.

For PET imaging, an imaging agent for diagnostic use containing the compound of the present invention is administered to a subject by injection, and radioactivity measurement is performed using a known PET scanner to determine the biodistribution and the accumulation intensity of the compound of the present invention.

Cancer tissues can be detected by comparison of the radioactivity levels among tissues, that is, tissues showing a relatively higher radioactivity level can be regarded as cancer tissues. For the comparison of the radioactivity levels, it is preferable to use SUV (Standardized Uptake Value), in particular SUV (tissue)/SUV (blood), which is a value relative to the blood radioactivity level. Alternatively, based on the image data, tissues showing a relatively higher radioactivity level may be regarded as cancer tissues.

The radioactive concentration of the radioactive imaging agent of the present invention for diagnostic use is not particularly limited as long as a sufficient level of radioactivity for measurement can be ensured by the radioactive concentration at the time of use, but preferred is 5 to 125 MBq, and more preferred is 10 to 100 MBq as the radioactive concentration at the time of use.

In addition, the compound of the present invention is considered to accumulate more intensively in cancer cells with a higher proliferation rate, and therefore can be used for evaluation of the malignancy of cancer. The malignancy of cancer can be evaluated by analyzing the radioactivity levels or the image data of cancer tissues. Tissues showing a relatively higher radioactivity level can be determined as more highly malignant (having a higher proliferation rate). The evaluation results on the malignancy of cancer can be used for confirmation of therapeutic effects, determination of the therapeutic strategy, etc.

The present invention further includes the following:

a method for cancer diagnosis, comprising administering an effective amount of the compound of the present invention to a mammal;

a PET diagnostic imaging method comprising administering an effective amount of the compound of the present invention to a mammal;

a method for detecting cancer tissues, comprising administering an effective amount of the compound of the present invention to a mammal;

a method for evaluating the malignancy of cancer, comprising administering an effective amount of the compound of the present invention to a mammal;

the compound of the present invention for use in cancer diagnosis;

the compound of the present invention for use in PET diagnostic imaging;

the compound of the present invention for use in detection of cancer tissues;

the compound of the present invention for use in evaluation of the malignancy of cancer;

use of the compound of the present invention for production of a medicine for cancer diagnosis; and use of the compound of the present invention for production of a PET imaging agent for diagnostic use.

EXAMPLES

Hereinafter, the present invention will be illustrated in detail by Examples, but is not limited thereto. In Examples, "room temperature" shall usually mean about 5 to 35° C.

Example 1: Synthesis of 2-amino-3-(5-(2-fluoroethoxy)-2-iodophenyl)propanoic acid According to the following scheme, 2-amino 3-(5-(2-fluoroethoxy)-2-iodophenyl)propanoic acid (compound 16 in Table 1) was synthesized.

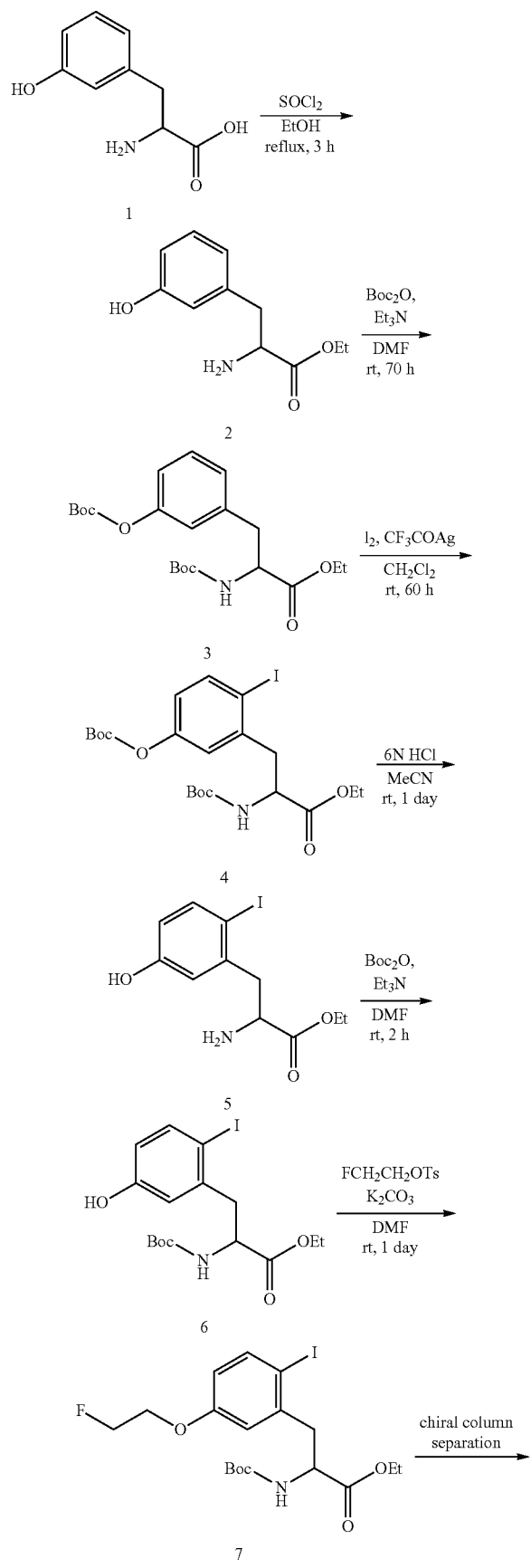
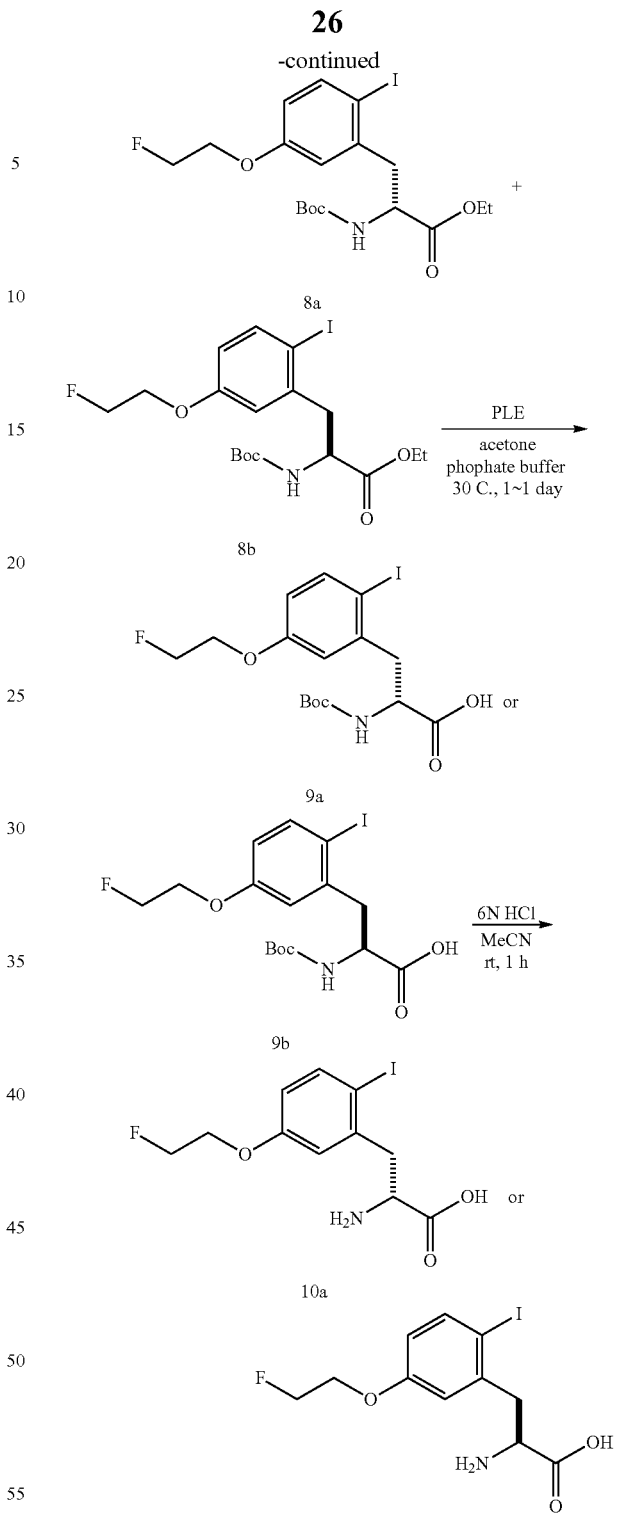
(1) Synthesis of Compound 3
To an ethanol (25 mL) solution of dl-m-tyrosine (1.0 g, 5.5 mmol), thionyl chloride (0.47 mL, 6.6 mmol) was added at 0° C., and the mixture was refluxed for 3 hours. The reaction mixture was allowed to come to room temperature, and the solvent was evaporated off in vacuo to give compound 2.

To a solution of compound 2 and triethylamine (3.1 mL, 22 mmol) in N,N-dimethylformamide (DMF) (4 mL), di-t-butyl dicarbonate (Boc₂O) (3.0 g, 13.7 mmol) was added at 0° C. The reaction mixture was stirred at room temperature for 70 hours, diluted with ethyl acetate, and washed with an aqueous sodium chloride solution (50 mL) twice. The aqueous layer was extracted with ethyl acetate (20 mL) twice. The combined extracts were dried over anhydrous sodium sulfate. After filtration, the solvent in the filtrate was evaporated off in vacuo, and the resulting crude product was purified by silica gel column chromatography to give compound 3 (yield: 1.69 g, 74.7%).

(2) Synthesis of Compound 4

Compound 3 (1 g, 2.4 mmol) and silver trifluoroacetate (0.65 g, 2.9 mmol) were suspended in dichloromethane (20 mL), iodine (0.68 g, 2.7 mmol) was added thereto with stirring under an argon atmosphere at room temperature, and stirring was continued at room temperature for 60 hours. After filtration of the reaction mixture, the solvent in the filtrate was evaporated off in vacuo, and the resulting crude product was purified by silica gel column chromatography (heptane/AcOEt-95/5 to 75/25) to give compound 4 (yield: 1.0 g, 76.5%).

(3) Synthesis of Compound 5

To an acetonitrile (10 mL) solution of compound 4 (535 mg, 1 mmol), 6 N hydrochloric acid (10 mL) was added under ice cooling. The reaction mixture was allowed to come to room temperature and then stirred for one day. After the completion of the reaction was confirmed by LC/MS monitoring, the reaction mixture was basified with a saturated sodium hydrogen carbonate solution, and extraction with ethyl acetate was performed 3 times. The organic layer was dried over anhydrous sodium sulfate and filtered, and the solvent in the filtrate was evaporated off in vacuo. The resulting light-yellow oil was purified by silica gel column chromatography (CHCl₃/MeOH=10/0 to 7/3) to give 2.29 g of a wet solid. The solid was washed with chloroform/heptane (1/9), and compound 5 was obtained as a white solid (yield: 2.13 g, 81%).

(4) Synthesis of Compound 6

To a solution of compound 5 (2.16 g, 6.44 mmol) and triethylamine (1.35 mL, 9.65 mmol) in anhydrous DMF (43 mL), Boc₂O (1.77 g, 7.72 mmol) was added. The reaction mixture was stirred at room temperature for 2 hours, 10 mL of purified water was added thereto, and the whole mixture was extracted with chloroform twice. The extract was dried over sodium sulfate and filtered, and the solvent in the filtrate was evaporated off in vacuo to give 3.79 g of a crude product. The ¹H-NMR analysis of the crude product confirmed the presence of compound 4 as a by-product. The obtained crude product was purified by silica gel column chromatography (CHCl₃/MeOH=10/0 to 9/1) to give compound 6 as a colorless oil (yield: 2.69 g, 96%). Compound 4, which was present in a small amount, was removed.

(5) Synthesis of 2-fluoroethyl tosylate

To an anhydrous pyridine (180 mL) solution of 2-fluoroethanol (11 mL, 187 mmol), tosyl chloride (40.9 g, 215 mmol) was added portionwise over 30 minutes or more under ice cooling. The reaction mixture was slowly heated to room temperature and then stirred for one day. The reaction was suppressed by addition of cold purified water (200 mL) and stirring was continued for 1 hour. After the whole mixture was extracted with ethyl acetate twice, the extract was washed with purified water (100 mL) and subsequently with 1M hydrochloric acid (250 mL) 4 times. The organic layer was washed with a saturated sodium hydrogen carbonate solution and subsequently with an aqueous sodium chloride solution, dried over anhydrous sodium sulfate and filtered, and the solvent in the filtrate was evaporated off in vacuo. The resulting oily crude product was purified by silica gel column chromatography (heptanes/AcOEt=8/2 to 5/5) to give 2-fluoroethyl tosylate as a colorless liquid (yield: 29.6 g, 73%).

(6) Synthesis of Compound 7

To a solution of compound 6 (2.65 g, 4.78 mmol, purity: 79%) and potassium carbonate (1.98 g, 14.4 mmol) in anhydrous DMF (33 mL), an anhydrous DMF (33 mL) solution of 2-fluoroethyl tosylate (2.085 g, 9.56 mmol) was added portionwise. The reaction mixture was stirred at room temperature for one day and then subjected to filtration through Celite (registered trademark), followed by washing with chloroform. The solvent in the filtrate was evaporated off in vacuo to give 5.28 g of an oily crude product. The crude product was purified by silica gel column chromatography (CHCl₃/MeOH=10/0 to 9/1) to give a wet solid. The solid was washed with chloroform/hexane (1/9), and 1.36 g of a white solid was obtained. The filtrate was also washed with the same solvent, and 289 mg of compound 7 was obtained. The remaining crude product (filtrate) was subjected to solvent evaporation in vacuo and subsequent purification by silica gel column chromatography (hexane/EtOH=99/1 to 9/1) to give 138 mg of compound 7. The total percentage yield of compound 7 was 78% or more.

(7) Optical Resolution of Compounds 8a and 8b

The optical resolution of compound 7 was performed on the following conditions.
Column type: chiralcel chiralpak IA (semi separative, manufactured by Daicel Corporation)
Eluent: hexane and EtOH=9/1
Elution speed: 15 mL/min
Column temperature: 25° C.
Detector: 233 nm (8) Synthesis of Compound 9a Compound 8a (61 mg, 0.127 mmol), acetone (0.5 mL) and a phosphate buffer of pH 7.0 (0.1M, 5 mL) were placed into a 100-mL round bottom flask and heated to 30° C. Porcine liver esterase (PLE) (17 units/mg, 15 mg) was added to the flask, and the reaction mixture was stirred at 30° C. for 1 to 2 days. As needed, porcine liver esterase was further added. After the completion of the reaction was confirmed by LC/MS monitoring, ethyl acetate (6 mL) was added to the reaction mixture and stirring was continued for 20 minutes. The resulting slurry was subjected to filtration through Celite (registered trademark), followed by sufficient washing with ethyl acetate, and solvent evaporation in vacuo was performed to give 68 mg of a crude product. The obtained crude product was subjected to the next step without purification.

Compound 9b was synthesized from compound 8b in the same procedure as for the synthesis of compound 9a.

(9) Synthesis of Compound 10a

To an acetonitrile (9.3 mL) solution of compound 9a (782 mg, approx. 1.73 mmol), 6 N hydrochloric acid (35 mL) was added under ice cooling. The reaction mixture was allowed to come to room temperature and then stirred for one hour. After the solvent in the reaction mixture was evaporated off in vacuo, the resulting crude solid was dissolved in purified water (10 mL), and the solution was basified with a saturated sodium hydrogen carbonate solution and then neutralized with 1 N hydrochloric acid. After the solvent in the solution was evaporated off in vacuo, the residue was purified by ODS column chromatography ($H_2O$/MeOH=95/5 to 20/80) to give 572 mg of a white solid. The solid was washed with heptane, and compound 10a was obtained as a white solid (yield: 559 mg, 92%). Compound 10b was synthesized from compound 9b in the same procedure as for the synthesis of compound 10a.

$^1$H-NMR (400 MHz, $D_2O$/DCl) δ7.62 (d, J=8.8 Hz, 1H), 6.77 (d, J=2.4 Hz, 1H), 6.55 (dd, J=2.4 Hz and 8.8 Hz, 1H), 4.62 (t, J=4.0 Hz, 1H), 4.50 (t, J=4.0 Hz, 1H), 4.17 (dd, J=7.2 Hz and 8.0 Hz, 1H), 4.10 (t, J=4.0 Hz, 1H), 4.03 (t, J=4.0 Hz, 1H), 3.24 (dd, J=7.2 Hz and 14.0 Hz, 1H), 3.04 (dd, J=8.0 Hz and 14.0 Hz, 1H). HRMS (FAB+): m/z Calcd. for $C_{11}H_{14}FINO_3$ [M+H]+ 352.9924. Found 353.9991.

The results of the measurement of compounds 10a and 10b using an optical isomer separation column are shown below.
HPLC Analysis Conditions:
Column: CROWNPAC CR (+) 4.0=Ø×150 mm (manufactured by Daicel Corporation)
Flow rate: 0.7 mL/min
Column oven temperature: 20° C.
Detection light wavelength: 233 nm
Eluent: pH 2 $HClO_4$ aqueous solution/methanol=85/15
Retention time: 77.3 min for compound 10a, 96.9 min for compound 10b Example 2: Evaluation of Activities of Compounds 10a and 10b to Specifically Accumulate in Cancer Cells A human LAT1 expression vector or a human LAT2 expression vector was transfected using Lipofectamine (registered trademark) 2000 (Invitrogen) into a human embryonic kidney cell line HEK293. G418-resistant HEK293 clones were selected, and among them, a clone showing human LAT1-specific amino acid uptake and a clone showing human LAT2-specific amino acid uptake were selected and established as a human LAT1 stably expressing cell line and a human LAT2 stably expressing cell line, respectively (Khunweeraphong et al. J Pharmacol Sci. 2012 Aug. 18; 119(4): 368-80. Epub 2012 Jul. 31).

The human LAT1 stably expressing cell line and the human LAT2 stably expressing cell line were seeded at $1.2×10^5$ cells/well on separate collagen-coated 24-well plates, and after 48 hours, the cells were washed 3 times with an uptake buffer ($Na^{2+}$-free Hank's balanced salt solution (HBSS), pH 7.4) prewarmed at 37° C. Compound 10a, compound 10b or a positive control FAMT (fluoro-α-methyltyrosine) was added at 100 μM, and incubation was performed at 37° C. for 3 minutes. Cells not treated with any of these compounds were used as a negative control. After the incubation, 1 μM of [$^{14}$C]L-leucine or [$^{14}$C]alanine was added to the wells, [$^{14}$C]L-leucine or [$^{14}$C]alanine uptake was allowed to proceed for 1 minute, and the cells were washed 3 times with an ice-cold uptake buffer. Subsequently, 500 μL of 0.1 M NaOH was added to each well for cell lysis, 20 μL of the lysate was used for the measurement of the protein concentration, and the remaining lysate was used for the measurement of the intracellular radioactivity. The measured radioactivity was normalized to the protein concentration, and on the assumption that the amino acid uptake activity in the negative control was 100%, the percentage (%) of inhibition of amino acid uptake in the presence of each compound was calculated.

In the presence of compound 10a, compound 10b or FAMT, the percentage of inhibition of amino acid uptake in the human LAT1 stably expressing cell line was higher than that in the human LAT2 stably expressing cell line. The percentages of inhibition of amino acid uptake in the human LAT1 stably expressing cell line were 52.4% for FAMT, 92.5% for one of compounds 10a and 10b, and 30.2% for the other. As shown in these results, one of compounds 10a and 10b far surpasses FAMT in the inhibitory performance on amino acid uptake, and the other is nearly equivalent to FAMT.

The compound for which the percentage of inhibition of amino acid uptake in the human LAT1 stably expressing cell line was 92.5% (this compound is called "the compound of Example 1" in Examples 3, 4 and 5) was used in the following Examples 3, 4 and 5.

Example 3: Inhibitory Effect on Leucine or Alanine Uptake in Human LAT1 Stably Expressing Cell Line and Human LAT2 Stably Expressing Cell Line Using the same cell lines as described in Example 2, the compound of Example 1 was examined for the inhibitory effect on leucine or alanine uptake in the human LAT1 stably expressing cell line and the human LAT2 stably expressing cell line in the same manner as in Example 2. FAMT was used as the positive control. The compound of Example 1 or FAMT was added at 100 μM. Cells not treated with either of these compounds were used as a negative control. On the assumption that the amino acid uptake activity in the negative control (control) was 100%, the percentage (%) of inhibition of amino acid uptake in the presence of FAMT or the compound of Example 1 was calculated. In addition, the cancer cell selectivity was calculated as the ratio of the amino acid uptake activity in the human LAT2 stably expressing cell line relative to that in the human LAT1 stably expressing cell line.

In another experiment, the cells were treated with the compound of Example 1 at eight different concentrations (0.1, 1, 3, 10, 30, 100, 300 and 1000 μM), and the concentration causing 50% inhibition of amino acid uptake was calculated as the $IC_{50}$ value.

The results are shown in Table 4. It is shown that the compound of Example 1 has a stronger inhibitory effect on [$^{14}$C]L-leucine uptake in the human LAT1 stably expressing cell line than FAMT and has a higher tendency to accumulate intensively in cancer cells than FAMT. Also shown is that the compound of Example 1 has a higher selectivity for cancer cells than FAMT.

TABLE 4

| | Percentage of inhibition* of LAT1-mediated amino acid uptake (%) | Percentage of inhibition* of LAT2-mediated amino acid uptake (%) | Cancer cell selectivity** |
|---|---|---|---|
| Control | 0.0 | 0.0 | — |
| FAMT | 52.4 | 28.3 | 1.5 |
| Example 1 | 92.5 | 55.1 | 6.0 |

*100 (%) − amino acid uptake activity (%) = percentage of inhibition (%)
**amino acid uptake activity in human LAT2 stably expressing cell line/amino acid uptake activity in human LAT1 stably expressing cell line The inhibitory effects of the compound of Example 1 on amino acid uptake in the human LAT1 stably expressing cell line and the human LAT2 stably expressing cell line are shown in FIG. 1. The $IC_{50}$ values for the compound of Example 1 were calculated to be 9.2 µM in the human LAT1 stably expressing cell line and 84.0 µM in the human LAT2 stably expressing cell line. Therefore, the compound of Example 1 was shown to be 9 times or more selective for LAT1 over LAT2.

The above results show that the compound of Example 1 has high selectivity for cancer, indicating that the compound of Example 1 accumulates more intensively in tumor sites than in normal sites when used for PET diagnosis of cancer.

Example 4: Promoting Effect on Leucine or Alanine Efflux from Human LAT1 Stably Expressing Cell Line and Human LAT2 Stably Expressing Cell Line In the same manner as in Example 3, the human LAT1 stably expressing cell line and the human LAT2 stably expressing cell line were seeded on separate collagen-coated 24-well plates, and after 48 hours, the cells were washed with an uptake buffer prewarmed at 37° C. An uptake buffer supplemented with 1 µM of [$^{14}$C]L-leucine or [$^{14}$C]L-alanine was added to each well, and [$^{14}$C]L-leucine or [$^{14}$C]L-alanine uptake by the cells was allowed to proceed at 37° C. for 10 minutes. The cells were washed with an uptake buffer prewarmed at 37° C., treated with the compound of Example 1 or the positive control FAMT at 1, 2, 3, 5, 10, 20, 50, 100 or 200 µM, and incubated at 37° C. for 1 minute, and the supernatants were collected. The radioactivity in each supernatant was measured as the radioactivity of the amino acid released from the cells. Subsequently, 500 µL of 0.1 M NaOH was added to each well for cell lysis, 20 µL of the lysate was used for the measurement of the protein concentration, and the remaining lysate was used for the measurement of the residual radioactivity in the cells. The sum of the residual radioactivity and the released radioactivity in each experiment was checked to confirm that there was no great difference in the total radioactivity incorporated into the cells at the preloading among the experiments. Since human LAT1 and human LAT2 are exchange transporters, the number of molecules of the released radioactive amino acid is equal to that of the test compound incorporated into the cells.

Figure 2:
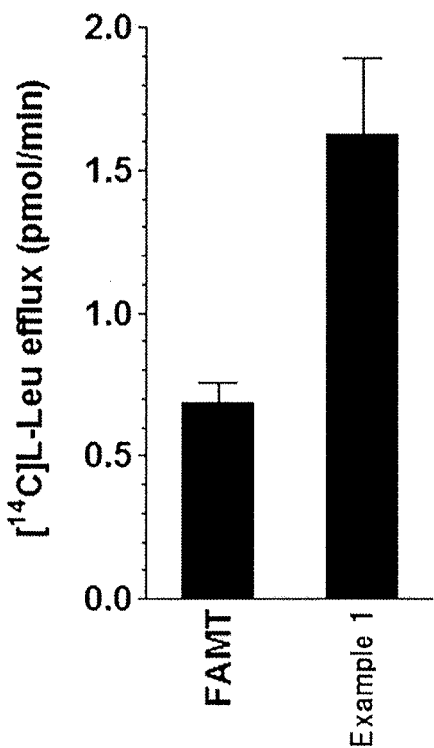
FIG. 2 shows the promoting effect of the compound of Example 1 on amino acid efflux from a human LAT1 stably expressing cell line.

The promoting effects on amino acid efflux from the human LAT1 stably expressing cell line in the presence of 10 µM of the compound of Example 1 or FAMT are shown in FIG. 2. As is clear from FIG. 2, the promoting effect of the compound of Example 1 on amino acid efflux via human LAT1 was twice or more higher than that of FAMT.

Based on the measured values of amino acid efflux at the indicated concentrations of each compound, the Km value for amino acid efflux from the human LAT1 stably expressing cell line and the Km value for amino acid efflux from the human LAT2 stably expressing cell line were calculated and shown in Table 5. As is clear from Table 5, the affinity of the compound of Example 1 for human LAT1 was 10 times or more higher than that of FAMT. These results indicate that the compound of Example 1 accumulates more intensively in tumor sites than FAMT when used for PET diagnosis of cancer.

TABLE 5

| Affinity for human LAT1 | |
|---|---|
| | Km (µM) |
| FAMT | 58.6 |
| Example 1 | 5.2 |

Example 5: Accumulation of Compound of Example 1 in Nude Mouse Bearing Subcutaneous Tumor Derived from Human Pancreatic Carcinoma Cell Line MIAPaCa-2

A tumor derived from subcutaneously implanted MIAPaCa-2 cells in a nude mouse was excised, and 0.1 g of the tumor was subcutaneously transplanted into a 6-week-old female nude mouse (BALB/cAJc1-nu). One month after the transplantation, the compound of Example 1 was dissolved in physiological saline at a concentration of 1 mM, and 0.1 mL (100 nmol) of the solution or 0.1 mL of physiological saline was administered from the tail vein. One hour after the administration, the tumor was excised, the amino acids in the tumor tissue were labeled with phenylisothiocyanate (PITC), and the labeled compound was detected by HPLC for evaluation of the accumulation.

Figure 3:
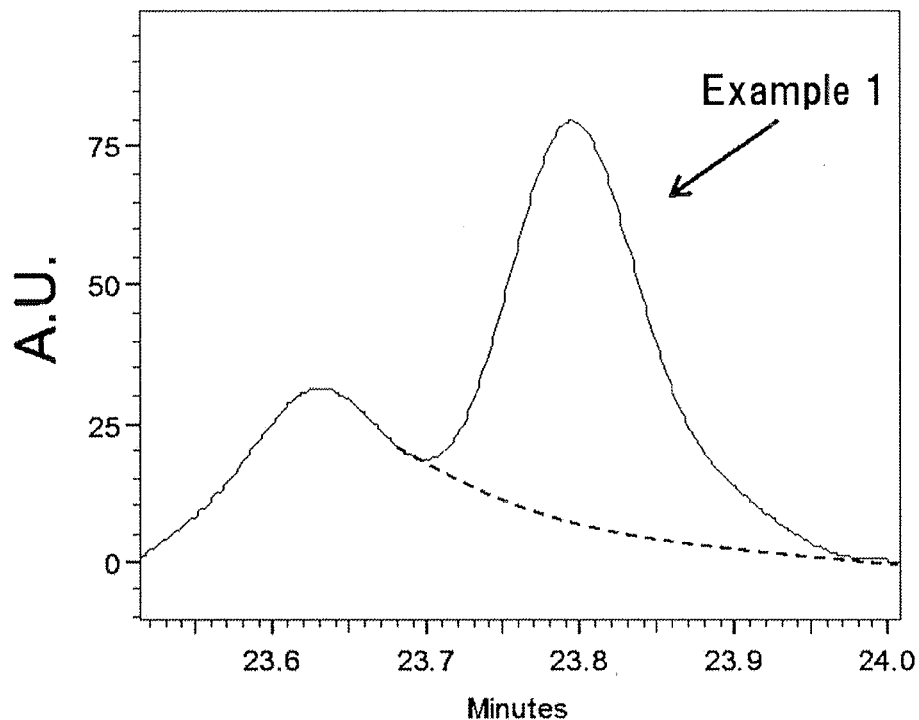
FIG. 3 is an HPLC chart showing the detection of the compound of Example 1 in a tumor excised from a subcutaneous tumor-bearing nude mouse treated with the compound of Example 1.

The results are shown in FIG. 3. As is clear from FIG. 3, the compound of Example 1 accumulated intensively in the tumor of the mouse treated with the compound of Example 1. These results demonstrate that the compound of Example 1 is excellent as a PET probe for tumor detection.

Example 6: Synthesis of 2-amino-3-(2-cyclopropyl-5-(2-fluoroethoxy)phenyl)propanoic acid According to the following scheme, 2-amino-3-(2-cyclopropyl-5-(2-fluoroethoxy)phenyl)propanoic acid (compound 1 in Table 1) was synthesized.

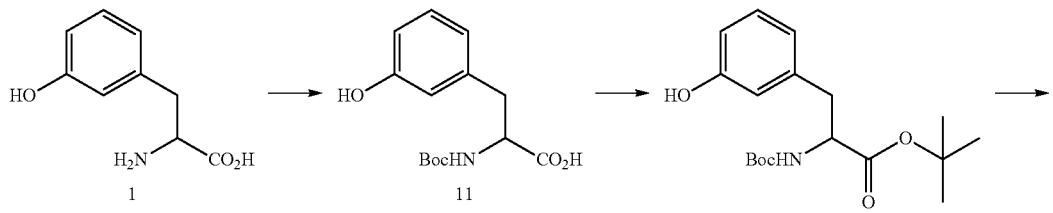

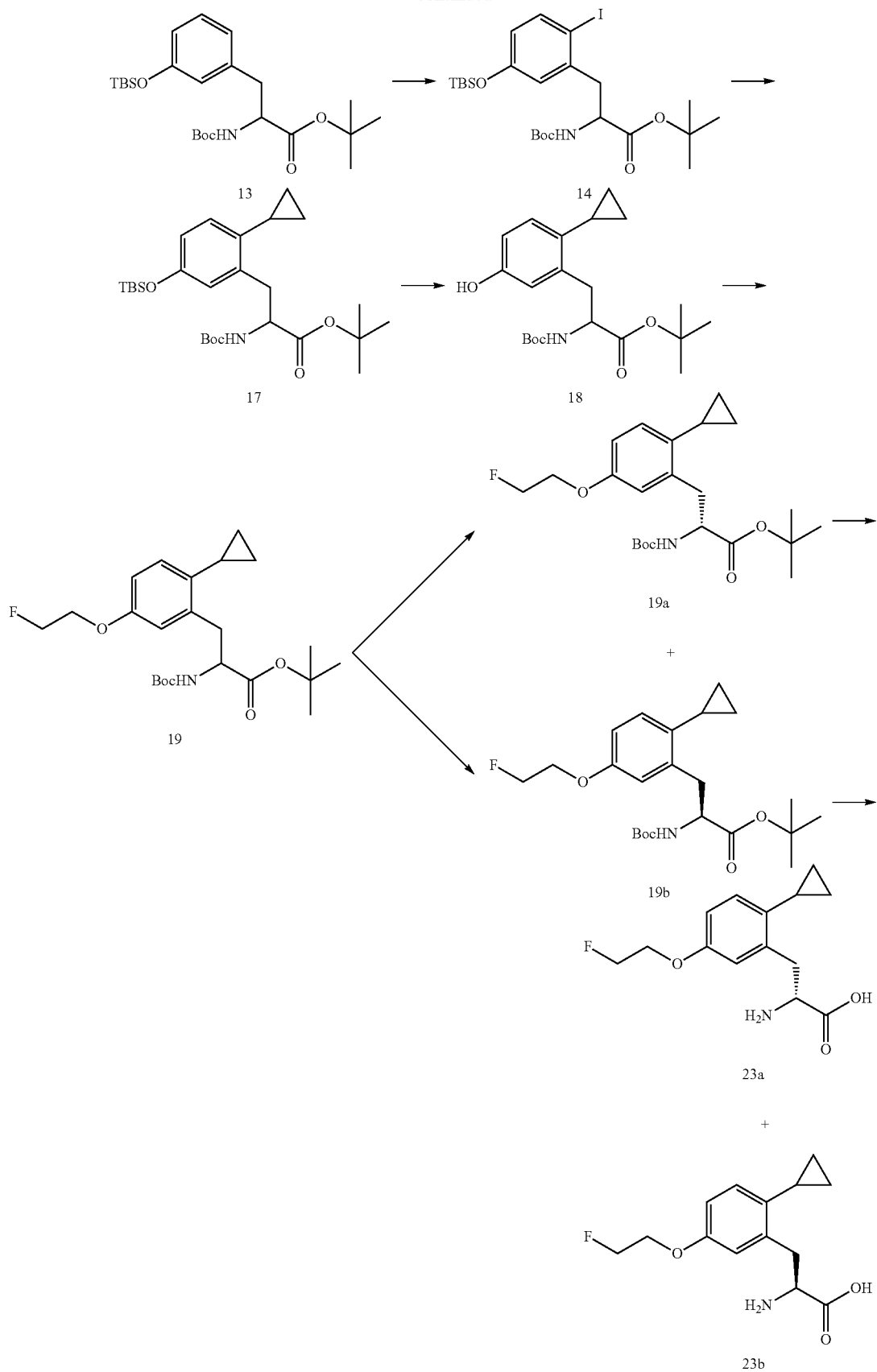

(1) Synthesis of Compound 11

To a solution containing dl-m-tyrosine (compound 1, 5.0 g, 27.6 mmol) and triethylamine (4.19 g, 41.4 mmol) in a dioxane/water (1/1) mixed solvent, Boc$_2$O (6.62 g, 30.4 mmol) was slowly added at 0° C., and the reaction mixture was stirred at 0° C. overnight. After the solvent in the reaction mixture was evaporated off in vacuo, a sodium hydrogen carbonate solution was added. The aqueous layer was washed with ethyl acetate, neutralized with hydrochloric acid, and extracted with ethyl acetate. The organic layers were combined, washed with a saturated aqueous sodium chloride solution, and dried over anhydrous sodium sulfate. After the solids were removed by filtration, the solvent in the filtrate was evaporated off in vacuo to give compound 11 as a colorless powder (yield: 7.5 g, percentage yield: 97%).

(2) Synthesis of Compound 12

Compound 11 (7.5 g, 26.7 mmol) obtained in the above (1) was dissolved in toluene (133 mL), and t-butyl alcohol (35 mL) was added thereto. The reaction mixture was heated under reflux, and N,N-dimethylformamide dineopentyl acetal (18.5 g, 21.7 mmol) was added dropwise over 55 minutes. After 3 hours of heating under reflux, the solution was cooled to room temperature and a saturated sodium hydrogen carbonate solution was added thereto. The aqueous layer was extracted with dichloromethane twice, and the resulting organic layer was dried over anhydrous sodium sulfate. After the solids were removed by filtration, the solvent in the filtrate was evaporated off in vacuo. The residue was purified with silica gel column chromatography to give compound 12 as a colorless powder (yield: 7.06 g, percentage yield: 78%).

(3) Synthesis of Compound 13

The protected tyrosine obtained in the above (2), i.e. compound 12 (6.03 g, 17.9 mmol), and imidazole (3.04 g, 44.6 mmol) were added to a DMF (36 mL) solution of TBSCl (3.23 g, 21.4 mmol) at 0° C., and the reaction mixture was heated to room temperature. Two hours later, the reaction mixture was diluted with water and extracted with ethyl acetate. The extract was washed with water and subsequently with a saturated aqueous sodium chloride solution, and then dried over anhydrous sodium sulfate. After filtration, the solvent was evaporated off in vacuo. The residue was purified by silica gel column chromatography to give compound 13 having a protected phenolic hydroxyl group (yield: 7.66 g, percentage yield: 95%).

(4) Synthesis of Compound 14

Compound 13 (452 mg, 1.0 mmol) obtained in the above (3) and silver trifluoroacetate (276 mg, 1.25 mmol) were added to chloroform (10 mL) to make a suspension, and iodine (317 mg, 1.25 mmol) was added thereto at −60° C., and stirring was continued at −60° C. for 5 days. After filtration of the reaction mixture, the filtrate was diluted with ethyl acetate and washed with an aqueous sodium thiosulfate solution and subsequently with a saturated aqueous sodium chloride solution. The organic layer was dried over anhydrous magnesium sulfate. After filtration, the solvent was evaporated off in vacuo. The residue was purified by silica gel column chromatography to give the desired compound 14 (yield of compound 14: 528 mg, percentage yield: 91%).

(5) Synthesis of Compound 17

Under an argon atmosphere, cyclopropyl zinc bromide (30 ml, 0.5 M THF solution) was added dropwise without stirring to a mixture of compound 14 (1.7 g, 3.0 mmol) obtained in the above (4), palladium acetate (67 mg, 0.3 mmol) and 2-dicyclohexyl-phosphino-2',6'-dimethoxybiphenyl (246 mg, 0.6 mmol). After the dropwise addition, stirring was started and the reaction mixture was heated to 40° C. Two hours later, the reaction mixture was allowed to cool down to room temperature, diluted with water and ethyl acetate, and filtered for removal of impurities. After extraction with ethyl acetate, the organic layer was washed with water and subsequently with a saturated aqueous sodium chloride solution, and dried over sodium sulfate. After filtration, the solvent was evaporated off in vacuo, and the residue was purified by silica gel column chromatography to give compound 17 (yield: 1.3 g, percentage yield: 87%).

(6) Synthesis of Compound 18

Compound 17 obtained in the above (5) was dissolved in THF, and tetrabutylammonium fluoride (TBAF) was added thereto at 0° C. After the reaction mixture was stirred for 1 hour, water was added thereto and extraction with ethyl acetate was performed twice. The organic layers were combined, washed with a saturated aqueous sodium chloride solution, and dried over anhydrous sodium sulfate. After filtration, the solvent was evaporated off in vacuo to give compound 18 (percentage yield: 96%).

(7) Syntheses of Compounds 19a and 19b

Compound 18 obtained in the above (6) was subjected to the same reaction as in Example 1 (6) to give compound 19 (percentage yield: 30%).

$^1$H-NMR (400 MHz, CDCl$_3$, TMS) δ6.98 (d, J=8.7 Hz, 1H), 6.72 (m, 2H), 5.02 (d, 9.1 Hz, 1H), 4.71 (dt, J=47.5 Hz and 4.1 Hz, H), 4.56 (m, 1H), 4.15 (dt, J=27.9 Hz and 4.1 Hz, 2H), 3.25 (m, 1H), 3.04 (m, 1H), 1.91 (m, 1H), 1.38 (s, 9H), 1.37 (s, 9H), 0.91 (m, 2H), 0.66 (m, 1H), 0.56 (m, 1H)

Optical resolution of the obtained racemic compound 19 was performed on the same conditions as in Example 1 (7) to give optically active compound 19a (>99% ee) and optically active compound 19b (>99% ee).

(8) Syntheses of Compounds 23a and 23b

Optically active compound 19a (200 mg, 0.5 mmol) obtained in the above (7) was dissolved in dichloromethane (1.6 mL), and to the solution, trifluoroacetic acid (0.8 mL) was added. The reaction mixture was stirred at room temperature for one day, and the solvent was evaporated off in vacuo. To the residue, water and an aqueous ammonia solution were added, and the solvent was evaporated off in vacuo. The residue was purified by silica gel column chromatography to give compound 23a (yield: 40 mg, percentage yield: 30%, >99% ee). The same reaction as above was performed using optically active compound 19b as the starting compound to give optically active compound 23b (percentage yield: 80%, >99% ee).

$^1$H-NMR (400 MHz, DCl/H$_2$O, DSS) δ7.08 (d, J=8.7 Hz, 1H), 6.91 (m, 2H), 4.79 (dt, J=47.4 Hz and 4.0 Hz, 2H), 4.44 (dd, J=8.9 and 6.6 Hz, 1H), 4.29 (dt, J=30.5 Hz and 4.0 Hz, 2H), 3.62 (m, 1H), 3.29 (m, 1H), 1.90 (m, 1H), 0.98 (m, 2H), 0.65 (m, 2H) HRMS (FAB+): m/z Calcd. for C$_{14}$H$_{19}$FNO$_3$ [M+H]+ 268.1349. Found 268.1361.

The results of the measurement of compounds 23a and 23b using an optical isomer separation column are shown below.

HPLC Analysis Conditions:
Column: CROWNPAC CR (+) 4.0 mmØ×150 mm (manufactured by Daicel Corporation)
Flow rate: 0.7 mL/min
Column oven temperature: 20° C.
Detection light wavelength: 233 nm
Eluent: pH 2 $HClO_4$ aqueous solution/methanol=85/15

Retention time: 76.5 min for compound 23a, 92.6 min for compound 23b

By the same method as in Example 9 shown below, 23a and 23b were determined to be an R-enantiomer and an S-enantiomer, respectively.

Example 7: Synthesis of 2-amino-3-(2-bromo-5-(2-fluoroethoxy)phenyl)propanoic acid According to the following scheme, 2-amino-3-(2-bromo-5-(2-fluoroethoxy)phenyl)propanoic acid (compound 12 in Table 1) was synthesized.

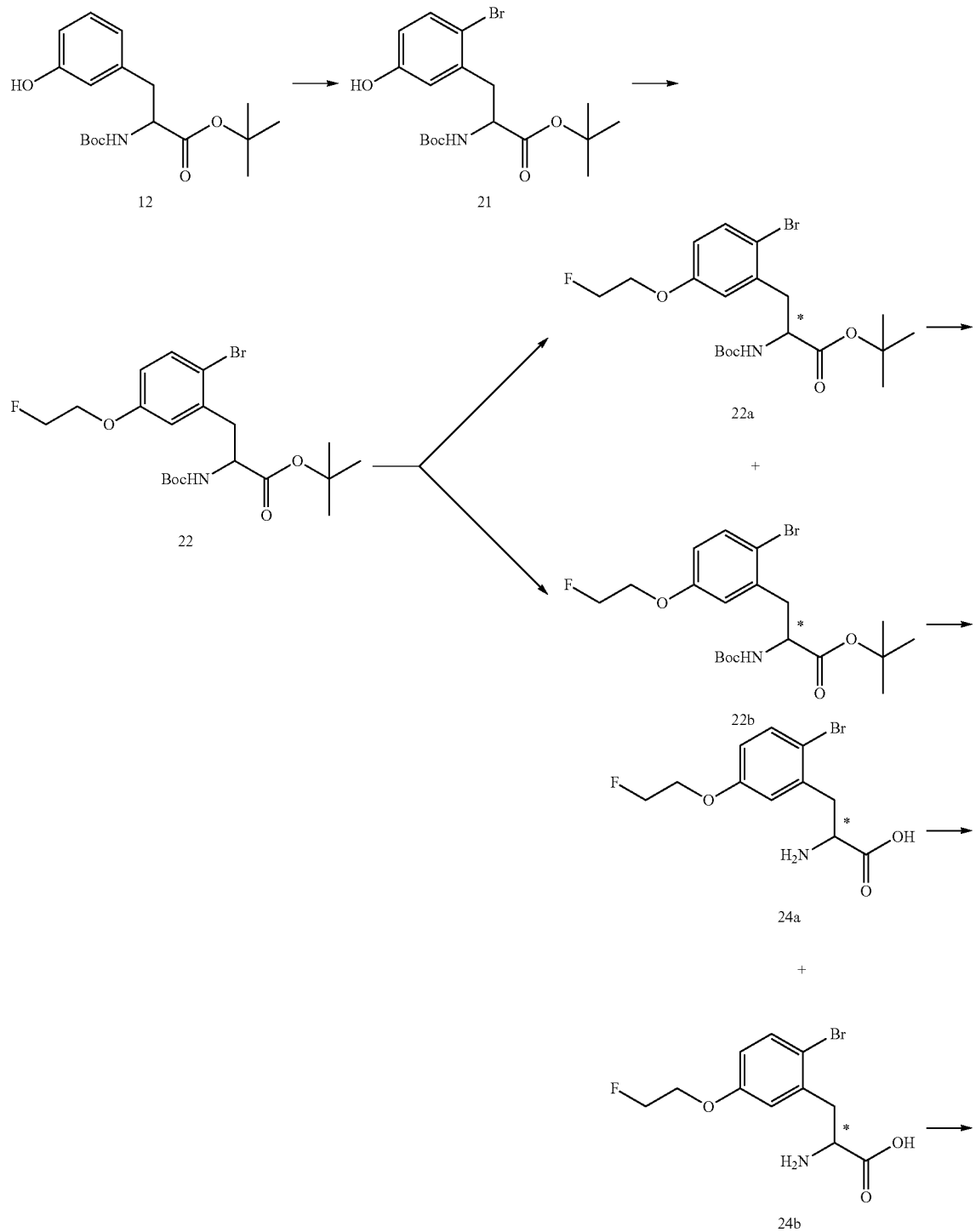

(1) Synthesis of Compound 21

Compound 12 (2.0 g, 5.9 mmol) obtained in the above Example 6 (2) was dissolved in DMF (20 mL), and to the solution, a DMF (10 mL) solution of N-bromosuccinimide (1.3 g, 7.1 mmol) was added dropwise over one hour under ice cooling under an argon atmosphere. After the dropwise addition, the reaction mixture was stirred at the same temperature for 5 hours. The reaction mixture was diluted with water and extracted with ethyl acetate 3 times. The organic layer was washed with water and subsequently with a saturated aqueous sodium chloride solution, and then dried. The solvent was evaporated off in vacuo and the residue was purified by silica gel column chromatography to give compound 21 (yield: 0.96 g, percentage yield: 39%).

(2) Syntheses of Compounds 22a and 22b

Compound 21 was subjected to the same reaction as in Example 1 (6) to give racemic compound 22 (percentage yield: 93%). $^1$H-NMR (400 MHz, CDCl$_3$, TMS) δ7.44 (d, J=8.7 Hz, 1H), 6.84 (s, 1H), 6.70 (dd, J=8.5 Hz, 2.5 Hz, 1H), 5.06 (m, 1H), 4.74 (dt, J=47.6 Hz and 4.1 Hz, 2H), 4.54 (m, 1H), 4.17 (dt, J=27.8 Hz and 4.2 Hz, 2H), 3.22 (m, 1H), 3.01 (m, 1H), 1.42 (s, 9H), 1.39 (s, 9H)

Compound 22 was subjected to optical resolution using a chiral column in the same manner as in Example 1 (7) to give compounds 22a (>99% ee) and 22b (>99% ee).

(3) Syntheses of Compounds 24a and 24b

Compounds 22a and 22b were subjected to the same reaction and work-up procedure as in Example 6 (8) to give compounds 24a (percentage yield: 81%, >99% ee) and 24b (percentage yield: 50%, >99% ee).
$^1$H-NMR (400 MHz, DCl/H$_2$O, DSS) δ7.61 (d, J=8.7 Hz, 1H), 7.02 (d, J=2.7 Hz, 1H), 6.93 (dd, J=8.9 and 3.0 Hz, 1H), 4.89 (m, 1H), 4.77 (m, 1H), 4.45 (dd, J=8.2 and 6.9 Hz, 1H), 4.36 (m, 1H), 4.29 (m, 1H), 3.51 (m, 1H), 3.29 (m, 1H). HRMS (FAB+): m/z Calcd. for C$_{11}$H$_{14}$BrFNO$_3$ [M+H]+ 306.0141. Found 306.0138.

The results of the measurement of compounds 24a and 24b using an optical isomer separation column are shown below.
HPLC Analysis Conditions:
Column: CROWNPAC CR (+) 4.0 mmØ×150 mm (manufactured by Daicel Corporation)
Flow rate: 0.7 mL/min
Column oven temperature: 20° C.
Detection light wavelength: 233 nm
Eluent: pH 2 HClO$_4$ aqueous solution/methanol=85/15
Retention time: 40.1 min for compound 24a, 51.1 min for compound 24b

Example 8: Synthesis of 2-amino-3-(5-(4-fluorobutoxy)-2-iodophenyl)propanoic acid According to the following scheme, 2-amino-3-(5-(4-fluorobutoxy)-2-iodophenyl)propanoic acid (compound 13 in Table 1) was synthesized.

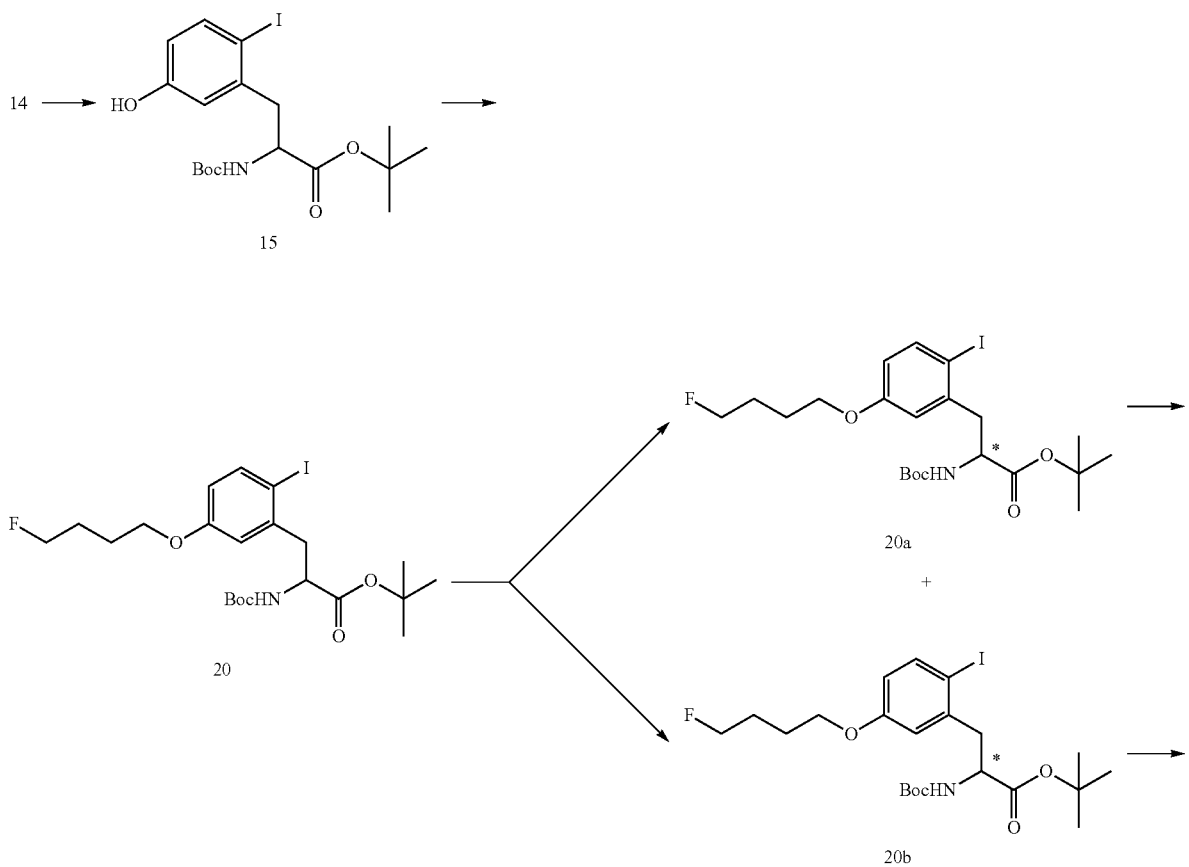

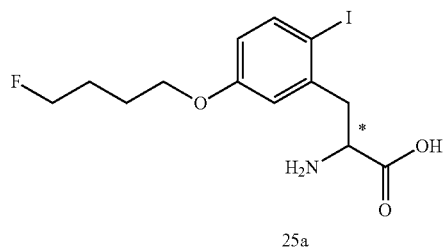

25a

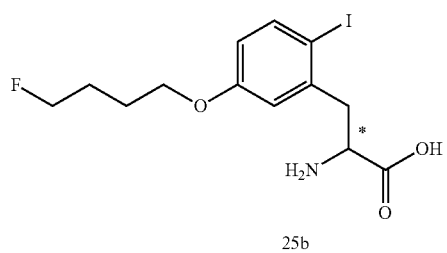

25b (1) Synthesis of Compound 15

Compound 14 (1.33 g, 2.3 mmol) obtained in the above Example 6 (4) was dissolved in THF (8 mL). To this solution, TEAR (3.5 mL, 1M THF solution) was added at 0° C., and the reaction mixture was stirred for 1 hour. After addition of water, extraction with ethyl acetate was performed twice. The organic layers were combined, washed with a saturated aqueous sodium chloride solution, and dried over anhydrous sodium sulfate. After filtration, the solvent was evaporated off in vacuo to give the desired compound 15 (yield: 1.03 g, percentage yield: 96%).

(2) Syntheses of Compounds 20a and 20b

Compound 15 was subjected to the same reaction as in Example 1 (6) using fluorobutyl tosylate instead of fluoroethyl tosylate, to give compound 20 (percentage yield: 69%).

$^1$H-NMR (400 MHz, CDCl$_3$, TMS) δ7.67 (d, J=8.7 Hz, 1H), 6.80 (s, 1H), 6.56 (dd, J=8.7 Hz and 2.7 Hz, 1H), 5.03 (m, 1H), 4.6-4.4 (m, 3H), 3.96 (t, J=5.9 Hz, 2H), 3.19 (m, 1H), 3.00 (m, 1H), 1.9-1.8 (m, 4H), 1.43 (s, 9H), 1.39 (s, 9H)

Compound 20 was subjected to optical resolution using a chiral column in the same manner as in Example 1 (7) to give compounds 20a (>99% ee) and 20b (>99% ee).

(3) Syntheses of Compounds 25a and 25b

Compounds 20a and 20b were subjected to the same reaction and work-up procedure as in Example 6 (8) to give compounds 25a and 25b.

$^1$H-NMR (400 MHz, DCl/H$_2$O, DSS) δ7.87 (d, J=8.7 Hz, 1H), 7.02 (d, J=3.2 Hz, 1H), 6.80 (dd, J=8.7 Hz and 3.2 Hz, 1H), 4.60 (dt, J=47.1 Hz and 5.7 Hz, 2H), 4.44 (dd, J=8.5 Hz and 7.1 Hz, 1H), 4.13 (t, J=6.2 Hz, 2H), 3.5 (m, 1H), 3.31 (m, 1H), 1.2-1.8 (m, 4H)

The results of the measurement of compounds 25a and 25b using an optical isomer separation column are shown below.

HPLC Analysis Conditions:

Column: CROWNPAC CR (+) 4.0 mmØ×150 mm (manufactured by Daicel Corporation)

Flow rate: 0.7 mL/min

Column oven temperature: 20° C.

Detection light wavelength: 233 nm

Eluent: pH 2 HClO$_4$ aqueous solution/methanol=85/15

Retention time: 106 min for compound 25a, 122 min for compound 25b

Example 9: Determination of Absolute Configurations of Compounds 10a and 10b

For determination of the absolute configurations of compounds 10a and 10b, the S-enantiomer of compound 10 (>99% ee) was synthesized according to the scheme shown below. Briefly, L-m-tyrosine was used as the starting compound and subjected to the same reaction as in the above Example 6.

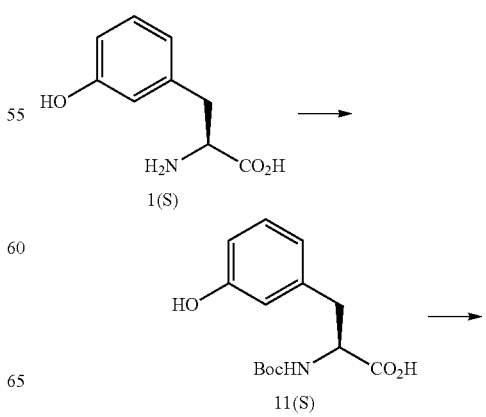

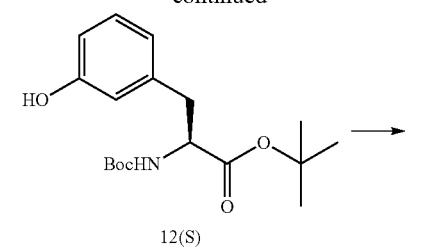

12(S)

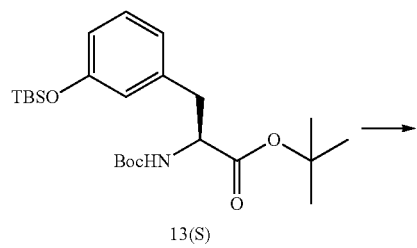

13(S)

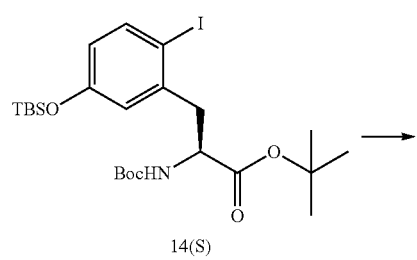

14(S)

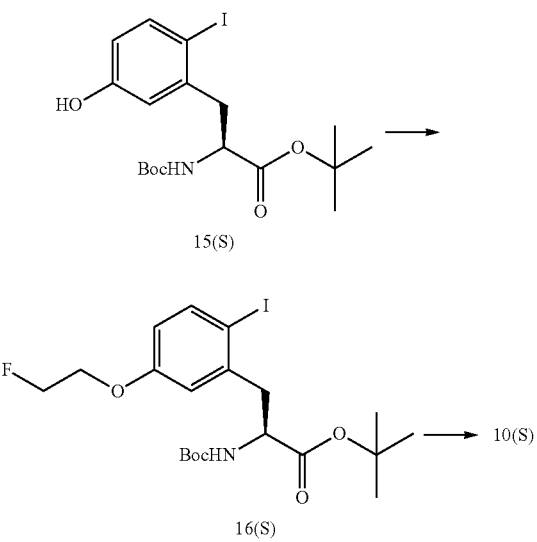

The retention time of the S-enantiomer was measured under the HPLC conditions shown in Example 1, and from the retention time, 10b was determined as an S-enantiomer. Based on this result, 10a was determined as an R-enantiomer.

Example 10: Synthesis of 2-amino-3-(5-(2-(2-fluoroethoxy)ethoxy)-2-iodophenyl)propanoic acid According to the following scheme, the S-enantiomer of 2-amino-3-(5-(2-(2-fluoroethoxy)ethoxy)-2-iodophenyl)propanoic acid (compound 6 in Table 1) was synthesized.

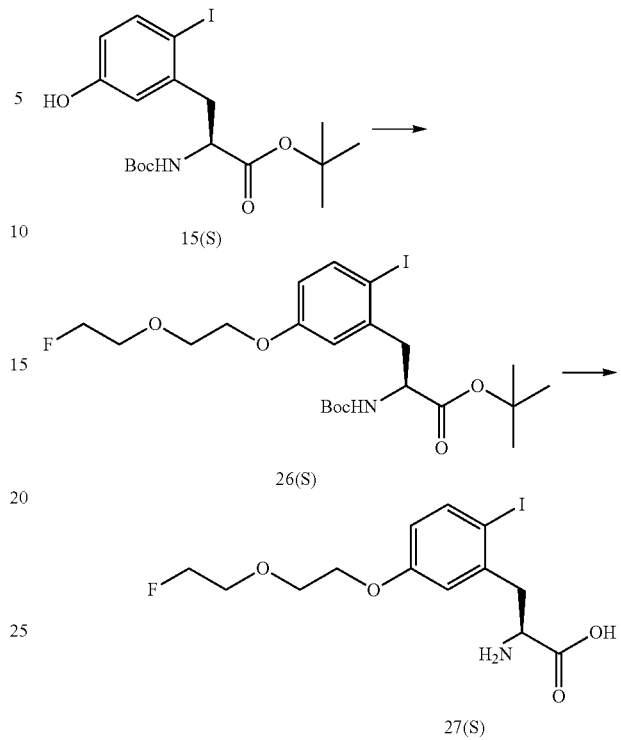

(1) Syntheses of Compounds 27 (S) and 27 (R)

Compound 15 (S) (S-enantiomer) was subjected to the same reaction as in Example 1 (6) using fluoroethoxyethyl tosylate instead of fluoroethyl tosylate, to give compound 26 (S) (S-enantiomer) (percentage yield: 78%). The protecting groups were removed from compound 26 (S) to give compound 27 (S) (S-enantiomer) (>99% ee). In the same manner, compound 27 (R) (R-enantiomer) was obtained from compound 15 (R) (R-enantiomer).

$^1$H-NMR (400 MHz, DCl/H$_2$O, DSS) δ7.89 (d, J=8.7 Hz, 1H), 7.04 (d, J=2.7, 1H), 6.81 (dd, J=8.7 Hz and 3.2 Hz, 1H), 4.66 (dt, J=47.6 Hz and 4.1 Hz, 2H), 4.45 (dd, J=8.7 Hz and 6.9 Hz, 1H), 4.24 (m, 2H), 3.95 (m, 2H), 3.88 (dt, J=31.6 Hz and 3.9 Hz, 2H), 3.51 (s, 1), 3.30 (S, 2H)

The results of the measurement of compounds 27 (S) and 27 (R) using an optical isomer separation column are shown below.

HPLC Analysis Conditions:
Column: CROWNPAC CR (+) 4.0 mmØ×150 mm (manufactured by Daicel Corporation)
Flow rate: 0.7 mL/min
Column oven temperature: 20° C.
Detection light wavelength: 233 nm
Eluent: pH 2 HClO$_4$ aqueous solution/methanol=85/15
Retention time: 84.7 min for compound 27 (R), 99.6 min for compound 27 (S)

Example 11: Synthesis of 2-amino-2-(4-(2-fluoroethoxy)phenyl)acetic acid

According to the following scheme, 2-amino-2-(4-(2-fluoroethoxy)phenyl)acetic acid (compound 69 in Table 3) was synthesized.

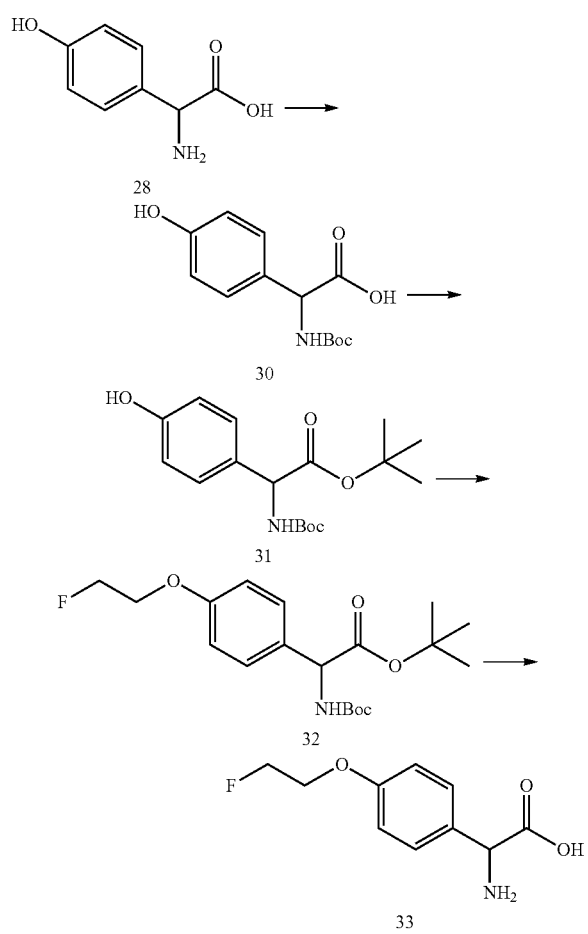

The same reaction as in Example 1 was performed using 4-hydroxyphenylglycine instead of dl-m-tyrosine, to give compound 30 (percentage yield: 99%). Next, tert-butyl esterification was performed in the same manner as in Example 6 (2) using compound 30 instead of compound 11, to give compound 31. Compound 31 was reacted with fluoroethyl tosylate in the same manner as previously described, and the protecting groups were removed to give the title compound (compound 33).

$^1$H-NMR (400 MHz, DCl/H$_2$O, DSS) δ7.39 (td, J=5.9 Hz and 3.7 Hz, 2H), 7.05 (td, J=5.9 Hz and 3.7 Hz, 2H), 5.14 (s, 1H), 4.76 (dt, J=47.4 Hz and 3.9 Hz, 2H), 4.29 (dt, J=30.5 Hz and 4.0 Hz, 2H). HRMS (FAB+): m/z Calcd. for C$_{10}$H$_{13}$FNO$_3$ [M+H]+ 214.0879. Found 214.0885.

Example 12: Synthesis of tert-butyl (2S)-2-(tert-butoxycarbonylamino)-3-(2-iodo-5-(2-(4-methylphenyl)sulfonyloxy)ethoxy)phenyl)propanoic acid (34 (S))

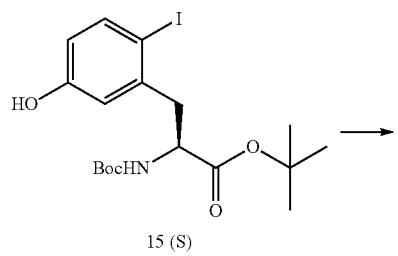

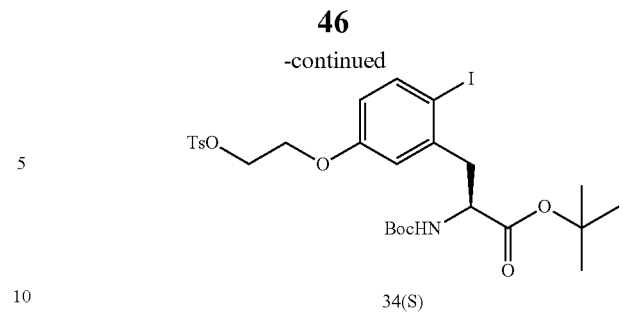

A solution of compound 15 (S) (0.6 g, 1.3 mmol), ethylene glycol di-p-tosylate (1.4 g, 3.9 mmol) and potassium carbonate (0.9 g, 6.5 mmol) in anhydrous DMF (10 ml) was stirred at room temperature for two days. After the completion of the reaction, the reaction mixture was diluted with water and extracted with ethyl acetate (approximately 20 mL) twice. The organic layers were combined, washed with water and subsequently with a saturated aqueous sodium chloride solution, and dried over magnesium sulfate. After filtration, the solvent was evaporated off in vacuo and the residue was purified by silica gel column chromatography to give compound 34 (S) (yield: 0.51 g, percentage yield: 59%, >99% ee). The same reaction as above was performed using optically active compound 15 (R) as the starting compound to give optically active compound 34 (R) (percentage yield: 57%, >99% ee).

$^1$H-NMR (400 MHz, CDCl$_3$, TMS) δ7.81 (dt, J=8.4 Hz and 1.9 Hz, 2H), 7.65 (d, J=8.7 Hz, 1H), 7.36 (d, J=7.8, 2H), 6.72 (s, 1H), 6.43 (dd, J=8.7 Hz, 1.8 Hz, 1H), 5.02 (m, 1H), 4.5 (m, 1H), 4.35 (m, 2H), 4.11 (m, 2H), 3.17 (m, 1H), 2.98 (m, 1H), 2.47 (s, 3H), 1.43 (s, 9H), 1.38 (s, 9H)

The results of the measurement of compounds 34 (S) and 34 (R) using an optical isomer separation column are shown below.

HPLC Analysis Conditions:

Column: CHIRALPAC IA 4.6 mmØ×250 mm (manufactured by Daicel Corporation)

Flow rate: 1.0 mL/min

Column oven temperature: 25° C.

Detection light wavelength: 254 nm

Eluent: Hexane/ethanol=60/40

Retention time: 9.3 min for compound 34 (R), 12.9 min for compound 34 (S)

Example 13: Synthesis of tert-butyl (2S)-2-(tert-butoxycarbonylamino)-3-(2-iodo-5-(2-(2-(4-methylphenyl)sulfonyloxy)ethoxyethoxy)phenyl)propanoic acid (35 (S))

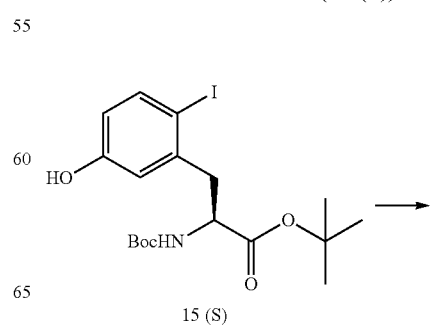

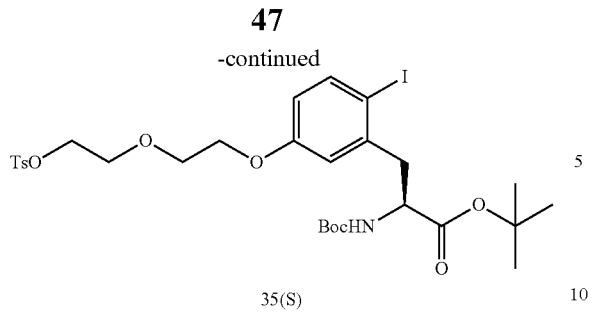

35(S)

The same reaction as in Example 12 was performed using diethylene glycol di-p-tosylate instead of ethylene glycol di-p-tosylate, to give optically active compound 35 (S) (percentage yield: 67%, >99% ee). The same reaction was performed using optically active compound 15 (R) as the starting compound to give optically active compound 35 (R) (percentage yield: 62%, >99% ee).

$^1$H-NMR (400 MHz, CDCl$_3$, TMS) δ7.80 (m, 2H), 7.67 (d, J=8.7 Hz, 1H), 7.32 (d, J=8.2 Hz, 2H), 6.81 (s, 1H), 6.53 (dd, J=8.5 Hz and 2.5 Hz, 1H), 5.09 (m, 1H), 4.5 (m, 1H), 4.19 (m, 2H), 4.01 (m, 2H), 3.76 (m, 4H), 3.19 (dd, J=14.0 Hz and 5.7 Hz, 1H), 2.98 (m, 1H), 2.44 (s, 3H), 1.43 (s, 9H), 1.38 (s, 9H)

The results of the measurement of compounds 35 (S) and 35 (R) using an optical isomer separation column are shown below.

HPLC Analysis Conditions:

Column: CHIRALPAC IB 4.6 mmØ×250 mm (manufactured by Daicel Corporation)

Flow rate: 1.0 mL/min

Column oven temperature: 25° C.

Detection light wavelength: 254 nm

Eluent: Hexane/ethanol=80/20

Retention time: 6.4 min for compound 35 (R), 7.1 min for compound 35 (S)

Example 14: Synthesis of tert-butyl 2-(tert-butoxycarbonylamino)-3-(2-bromo-5-(2-(4-methylphenyl)sulfonyloxy)ethoxy)phenyl)propanoate (36)

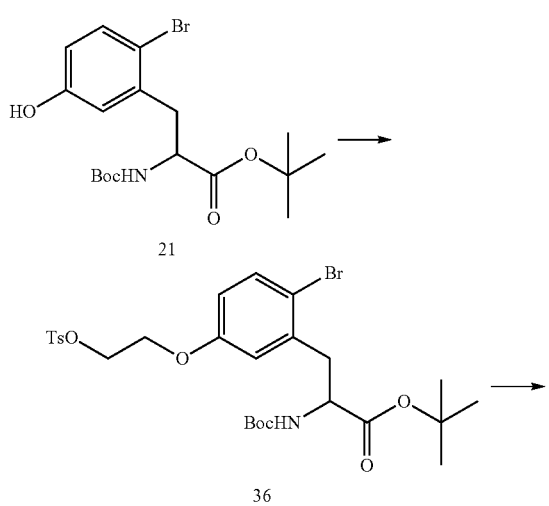

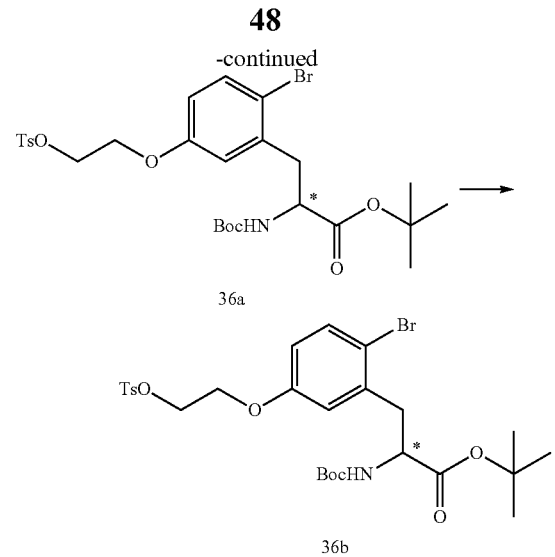

Compound 21 obtained in Example 7 was subjected to the same reaction as in Example 12 to give compound 36 (percentage yield: 74%).

$^1$H-NMR (400 MHz, CDCl$_3$, TMS) δ7.82 (dt, J=8.4 Hz and 1.9 Hz, 2H), 7.39 (d, J=8.8 Hz, 1H), 7.36 (d, J=7.6 Hz, 2H), 6.71 (s, 1H), 6.56 (m, 1H), 5.04 (m, 1H), 4.51 (m, 1H), 4.34 (m, 2H), 4.11 (m, 2H), 3.19 (dd, J=14.2 Hz and 5.9 Hz, 1H), 2.99 (m, 1H), 2.47 (s, 3H), 1.42 (s, 9H), 1.38 (s, 9H)

Optical resolution of compound 36 was performed by HPLC using a chiral column, and the isomers were separately recrystallized from hexane/ethyl acetate to give optically active compounds 36a (>99% ee) and 36b (>99% ee).

The results of the measurement of compounds 36a and 36b using an optical isomer separation column are shown below.

HPLC Analysis Conditions:

Column: CHIRALPAC IA 4.6 mmØ×250 mm (manufactured by Daicel Corporation)

Flow rate: 1.0 mL/min

Column oven temperature: 25° C.

Detection light wavelength: 254 nm

Eluent: Hexane/ethanol=70/30

Retention time: 11.6 min for compound 36a, 15.1 min for compound 36b

Example 15: Evaluation of Activities to Specifically Accumulate in Cancer Cells

The test compounds used in this Example were compounds 10a and 10b, which were synthesized in Example 1; compounds 23a and 23b, which were synthesized in Example 6; compounds 24a and 24b, which were synthesized in Example 7; compounds 25a and 25b, which were synthesized in Example 8; and compounds 27 (S) and 27 (R), which were synthesized in Example 10.

A human LAT1 stably expressing cell line and a human LAT2 stably expressing cell line, each of which was the same as described in Example 2, were seeded at 1.2×10$^5$ cells/well, and after 48 hours, the cells were washed 3 times with an uptake buffer (Na$^{2+}$-free Hank's balanced salt solution (HBSS), pH 7.4) prewarmed at 37° C. The test compounds, L-tyrosine or the positive control FAMT (fluoro-α-methyltyrosine) was added at 30 μM, and incubation was performed at 37° C. for 3 minutes. Cells not treated with any of these compounds were used as a negative control. After the incubation, 1 μM of [$^{14}$C]L-leucine or [$^{14}$C]alanine was added to the wells, [$^{14}$C]L-leucine or [$^{14}$C]alanine uptake was allowed to proceed for 1 minute, and the cells were washed 3 times with an ice-cold uptake buffer. Subsequently, 500 μL of 0.1 M NaOH was added to each well for cell lysis, 20 μL of the lysate was used for the measurement of the protein concentration, and the remaining lysate was used for the measurement of the intracellular radioactivity. The measured radioactivity was normalized to the protein concentration, and on the assumption that the amino acid uptake activity in the negative control was 100%, the percentage (%) of inhibition of amino acid uptake in the presence of each compound was calculated.

Figure 4:
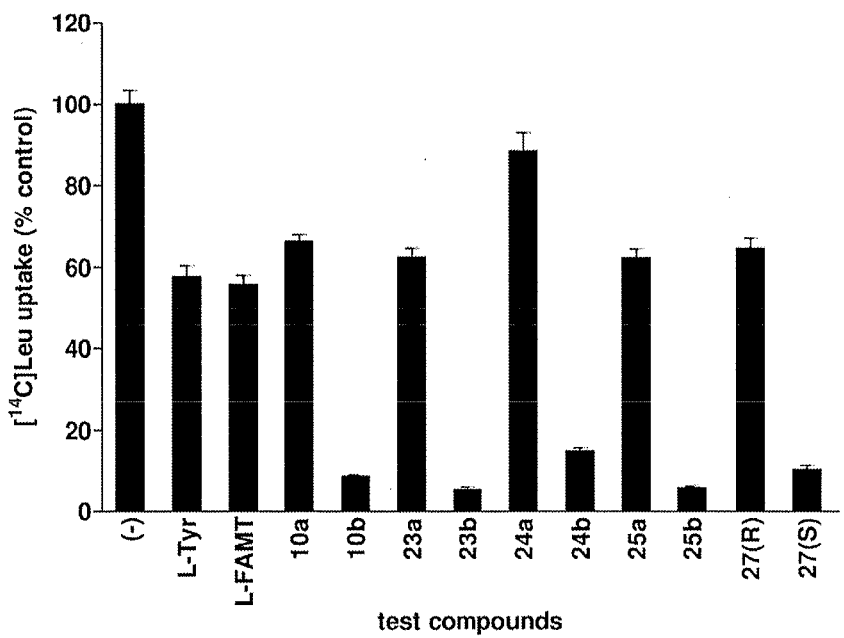
FIG. 4 shows the inhibitory effects of 10 test compounds on amino acid uptake in a human LAT1 stably expressing cell line.
Figure 5:
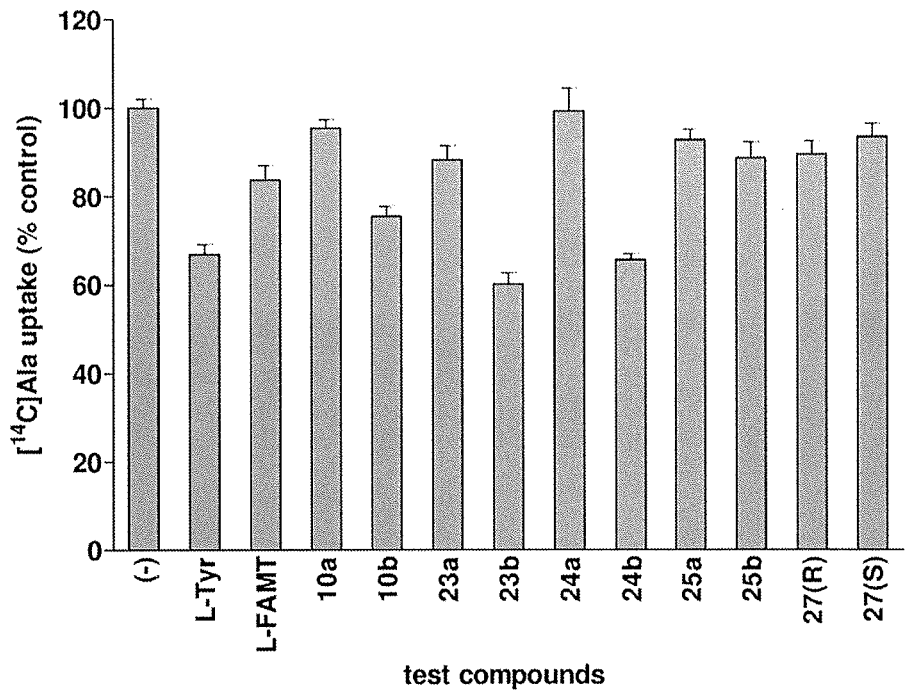
FIG. 5 shows the inhibitory effects of 10 test compounds on amino acid uptake in a human LAT2 stably expressing cell line.

The inhibitory effects on amino acid uptake in the human LAT1 stably expressing cell line are shown in FIG. 4, and the inhibitory effects on amino acid uptake in the human LAT2 stably expressing cell line are shown in FIG. 5. As shown in FIGS. 4 and 5, in the presence of each test compound or FAMT, the percentage of inhibition of amino acid uptake in the human LAT1 stably expressing cell line was higher than that in the human LAT2 stably expressing cell line, and all the test compounds are more prone to be incorporated into cancer cells than into normal cells.

In addition, the percentages of inhibition of amino acid uptake in both cells and the cancer cell selectivity (amino acid uptake activity in human LAT2 stably expressing cell line/amino acid uptake activity inhuman LAT1 stably expressing cell line) are shown in Table 6. As shown in the results, each of the test compounds has an equal or stronger activity to specifically inhibit cancer cell amino acid uptake than FAMT, and among them, compounds 10b, 23b, 24b, 25b and 27 (S) have a remarkably higher selectivity for cancer cells than FAMT. These results show that these compounds are expected to show equal or better performance in PET imaging than FAMT in terms of the cancer specificity and selectivity, and therefore useful for cancer diagnosis.

TABLE 6

| | Percentage of inhibition* of LAT1-mediated amino acid uptake (%) | Percentage of inhibition* of LAT2-mediated amino acid uptake (%) | Cancer cell selectivity** |
|---|---|---|---|
| Control | 0.0 | 0.0 | 1 |
| L-Tyr | 42.3 | 33.1 | 1.16 |
| L-FAMT | 44.2 | 16.3 | 1.5 |
| 10a | 33.8 | 4.7 | 1.44 |
| 10b | 91.2 | 24.5 | 8.59 |
| 23a | 37.5 | 11.8 | 1.41 |
| 23b | 94.5 | 39.9 | 11.2 |
| 24a | 11.6 | 0.8 | 1.12 |
| 24b | 85.1 | 34.3 | 4.42 |
| 25a | 37.7 | 7.3 | 1.49 |
| 25b | 94.1 | 11.3 | 15.13 |
| 27 (R) | 35.4 | 10.6 | 1.39 |
| 27 (S) | 89.5 | 6.5 | 9.04 |

*100 (%) − amino acid uptake activity (%) = percentage of inhibition (%)
**amino acid uptake activity in human LAT2 stably expressing cell line/amino acid uptake activity in human LAT1 stably expressing cell line Example 16: Promoting Effects on Leucine or Alanine Efflux from Human LAT1 Stably Expressing Cell Line and Human LAT2 Stably Expressing Cell Line The experiments in this Example were performed using the same 10 test compounds as used in Example 15 in the same manner as in Example 4. Based on the measured values of amino acid efflux at the indicated concentrations of each compound, the Km value for amino acid efflux from the human LAT1 stably expressing cell line and the Km value for amino acid efflux from the human LAT2 stably expressing cell line were calculated and shown in Table 7. As shown in this table, each test compound has a higher affinity for the human LAT1 stably expressing cell line than for the human LAT2 stably expressing cell line, and therefore has cancer selectivity. Also shown is that each test compound has a higher affinity for the human LAT1 stably expressing cell line than FAMT. These results show that the test compounds are expected to show equal or better performance in PET imaging than FAMT in terms of the cancer selectivity and the intensive accumulation in cancer, and therefore useful particularly for cancer diagnosis.

TABLE 7

| | Human LAT1 Km (μM) | Human LAT2 Km (μM) |
|---|---|---|
| L-Tyr | 31.0 | 32.7 |
| FAMT | 58.6 | 76.4 |
| 10a | 17.0 | 29.2 |
| 10b | 5.2 | 70.7 |
| 23a | 24.9 | 29.2 |
| 23b | 6.4 | 53.9 |
| 24a | 21.5 | 31.0 |
| 24b | 6.5 | 68.8 |
| 25a | 16.2 | 30.9 |
| 25b | 5.7 | 88.0 |
| 27 (R) | 17.3 | 26.2 |
| 27 (S) | 5.7 | 82.5 |

Example 17: Synthesis of $^{18}$F-Labeled Compound 10b

Proton beams were accelerated to 12 MeV by cyclotron HM12 (manufactured by Sumitomo Heavy Industries, Ltd.) and targeted to [$^{18}$O]H$_2$O with an isotopic purity of 95% or more to produce $^{18}$F$^-$ ($^{18}$F anion). The resulting solution was loaded onto an anion exchange resin column (Sep-pak QMA plus cartridge column) to trap $^{18}$F$^-$, and the trapped $^{18}$F$^-$ was eluted with a mixed solution of 33 mM K$_2$CO$_3$ and 33 mg/mL Kryptofix 222 (K2.2.2). Into a 10-mL vial, 700 μL (25 GBq) of the $^{18}$F-containing K$_2$CO$_3$/K2.2.2 solution was collected, and the water in the vial was completely removed by spraying helium gas with hot-air heating (110° C.) Subsequently, acetonitrile was added and then removed under the same heating conditions as above. This procedure was repeated 3 times to dehydrate the inside of the vial. To this was added an acetonitrile solution (0.5 mL) of compound 34 (S) (4.0 mg) obtained in Example 12 as a precursor for labeling, and the reaction mixture was stirred with heating at 110° C. for 10 minutes. Subsequently, a mixed solution (4.0 mL) of 5 M hydrochloric acid and acetonitrile (or methanol) in equal amounts was added thereto and the reaction mixture was stirred with heating for another 10 minutes. The reaction mixture was subjected to a semi preparative HPLC (column: Inertsil (registered trademark) ODS-3 (10×250 mm), mobile phase: MeCN/100 mM hydrochloric acid solution=30/70, flow rate: 2.0 mL/min), and the radioactive peak corresponding to the $^{18}$F-labeled compound 10b, which is typically eluted in approximately 7 minutes, was isolated. The decay corrected radiochemical yield calculated from the radioactivity of the obtained fraction was about 30%.

The preparative HPLC fraction containing the $^{18}$F-labeled compound 10b produced by radiosynthesis was recovered, the solvent in the fraction was evaporated off using a rotary evaporator with heating at 200° C., and the obtained $^{18}$F-labeled compound 10b was dissolved in a physiological saline to prepare a $^{18}$F-labeled compound 10b-containing physiological saline. The radiochemical purity of the prepared radiopharmaceutical solution was 95% or more.

Example 18: Examination of Intensive Accumulation of $^{18}$F-Labeled Compound 10b in Cancer The $^{18}$F-labeled compound 10b (12.5 MBq) was administered via the tail vein of a nude mouse bearing a tumor derived from subcutaneously implanted MIAPaCa-2 cells. PET imaging was performed using Inveon PET/CT (manufactured by Siemens) under inhalation anesthesia with isoflurane and oxygen. The imaging was performed for 10 minutes from 60 minutes after the tail vein injection. The acquired data were reconstructed by the 3D-OSEM (ordered subset expectation maximization) method.

Figure 6:
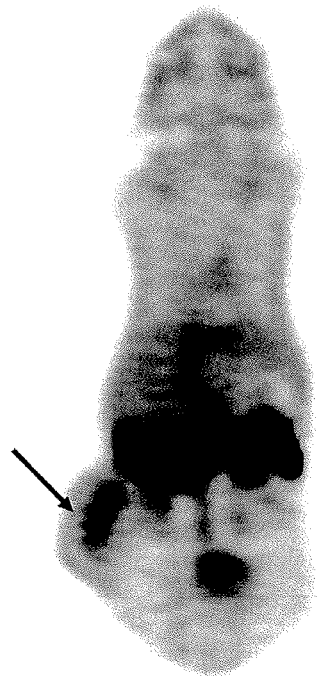
FIG. 6 shows the results of the examination of intensive accumulation of $^{18}$F-labeled compound 10b in cancer using a subcutaneous tumor-bearing nude mouse.

The results are shown in FIG. 6. The arrow in FIG. 6 shows a tumor site. As is clear from FIG. 6, intensive accumulation of the $^{18}$F-labeled compound 10b in the tumor site was observed. The results show that the compound of the present invention developed and evaluated by in vitro assays is applicable to PET imaging diagnosis of cancer.

The present invention is not limited to particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A compound of formula (I):

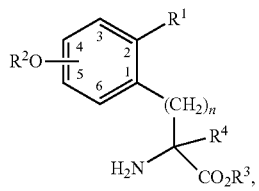

(I)

wherein n is 0 or 1;
R$^1$ is a nonradioactive halogen atom, a C1-C6 alkyl group, a C1-C6 haloalkyl group, an optionally substituted phenyl group, a C1-C6 alkylthio group, a C1-C6 alkoxy group, a C1-C6 haloalkoxy group or a C7-C12 aralkyloxy group;
R$^2$ is —(CH$_2$)$_p$—[O(CH$_2$)$_q$]$_r$—X (wherein X is a fluorine atom, p is an integer of 1 to 6, q is an integer of 1 to 4, and r is an integer of 0 to 4);
—OR$^2$ is at the 4 or 5 position of the benzene ring;
R$^3$ is a hydrogen atom; and
R$^4$ is a hydrogen atom or a C1-C6 alkyl group, or a pharmaceutically acceptable salt thereof.

2. The compound according to claim 1 or a pharmaceutically acceptable salt thereof, wherein the compound has an activity to specifically accumulate in cancer cells.

3. The compound according to claim 1 or a pharmaceutically acceptable salt thereof, wherein the compound is selected from the group consisting of:
2-amino-3-(5-(2-fluoroethoxy)-2-iodophenyl)propanoic acid and
2-amino-3-(2-cyclopropyl-5-(2-fluoroethoxy)phenyl)propanoic acid.

4. The compound according to claim 1 or a pharmaceutically acceptable salt thereof, wherein the compound is selected from the group consisting of:
2-amino-3-(2-bromo-5-(2-fluoroethoxy)phenyl)propanoic acid,
2-amino-3-(5-(4-fluorobutoxy)-2-iodophenyl)propanoic acid and
2-amino-3-(5-(2-(2-fluoroethoxy)ethoxy)-2-iodophenyl)propanoic acid.

5. The compound according to claim 1 or a pharmaceutically acceptable salt thereof, wherein the compound has a radioactive fluorine atom.

6. The compound according to claim 1 or a pharmaceutically acceptable salt thereof, wherein the compound of formula (I) is an optically active compound or a mixture of optically active compounds.

7. A pharmaceutical composition comprising the compound according to claim 1 or a pharmaceutically acceptable salt thereof, and a pharmaceutically acceptable carrier.

8. An optically active compound of formula (II):

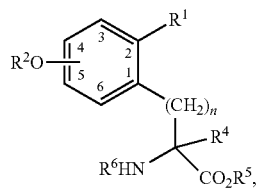

(II)

wherein n is 0 or 1;
R$^1$ is a nonradioactive halogen atom, a C1-C6 alkyl group, a C1-C6 haloalkyl group, an optionally substituted phenyl group, a C1-C6 alkylthio group, a C1-C6 alkoxy group, a C1-C6 haloalkoxy group or a C7-C12 aralkyloxy group;
R$^2$ is —(CH$_2$)$_p$—[O(CH$_2$)$_q$]$_r$—Y (wherein Y is a leaving group, p is an integer of 1 to 6, q is an integer of 1 to 4, and r is an integer of 0 to 4);
—OR$^2$ is at the 4 or 5 position of the benzene ring;
R$^4$ is a hydrogen atom or a C1-C6 alkyl group;
R$^5$ is a hydrogen atom or a protecting group for a carboxyl group; and
R$^6$ is a hydrogen atom or a protecting group for an amino group,
or a pharmaceutically acceptable salt thereof.

9. The compound according to claim 1 or a pharmaceutically acceptable salt thereof, wherein n is 1.

10. The compound according to claim 8 or a pharmaceutically acceptable salt thereof, wherein n is 1, and R$^1$ is a nonradioactive halogen atom, a C1-C6 alkyl group, a C1-C6 haloalkyl group, an optionally substituted phenyl group, a C1-C6 alkylthio group, a C2-C6 alkoxy group, a C1-C6 haloalkoxy group or a C7-C12 aralkyloxy group.

11. A positron emission tomography diagnostic imaging method comprising administering, to a mammal, an effective amount of the compound according to claim 5 or a pharmaceutically acceptable salt thereof, and imaging the mammal with positron emission tomography.

12. A method for detecting a cancer tissue, comprising administering, to a mammal, an effective amount of the compound according to claim 5 or a pharmaceutically acceptable salt thereof, and detecting a cancer tissue.

13. A method for evaluating the malignancy of a cancer, comprising administering, to a mammal, an effective amount of the compound according to claim 5 or a pharmaceutically acceptable salt thereof, and evaluating the malignancy of a cancer.

14. The compound according to claim 1 or a pharmaceutically acceptable salt thereof, wherein X is a radioactive fluorine atom.

* * * * *